US009389232B2

(12) United States Patent
Poland et al.

(10) Patent No.: US 9,389,232 B2
(45) Date of Patent: Jul. 12, 2016

(54) VACCINIA VIRUS POLYPEPTIDES

(71) Applicant: Mayo Foundation for Medical Education and Research, Rochester, MN (US)

(72) Inventors: Gregory A. Poland, Rochester, MN (US); Inna G. Ovsyannikova, Rochester, MN (US); Kenneth Lee Johnson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/173,550

(22) Filed: Feb. 5, 2014

(65) Prior Publication Data
US 2014/0220602 A1     Aug. 7, 2014

Related U.S. Application Data

(63) Continuation of application No. 13/222,862, filed on Aug. 31, 2011, now abandoned.

(60) Provisional application No. 61/379,311, filed on Sep. 1, 2010.

(51) Int. Cl.
*C07K 14/005* (2006.01)
*G01N 33/569* (2006.01)
*A61K 39/00* (2006.01)

(52) U.S. Cl.
CPC ........ *G01N 33/56983* (2013.01); *C07K 14/005* (2013.01); *A61K 39/00* (2013.01); *C12N 2710/24122* (2013.01); *C12N 2710/24134* (2013.01); *G01N 2333/07* (2013.01)

(58) Field of Classification Search
None
See application file for complete search history.

(56) References Cited

U.S. PATENT DOCUMENTS

2003/0157135 A1  8/2003  Tsuji et al.
2012/0076810 A1  3/2012  Poland et al.

OTHER PUBLICATIONS

Krishna et al. Tetrameric cell-surface MHC class I molecules. Nature. May 14, 1992;357(6374):164-7.*
"HLA Peptide Binding Predictions," Bioinformatics and Molecular Analysis Section, National Institute of Health [online] 1994, [retrieved on Jun. 6, 2013] Retrieved from the Internet, <URL: http://www-bimas.cit.nih.gov/molbio/hla_bind/> 1 page.
"NetMHC 3.0 Server," Center for Biological Sequence Analysis, Technical University of Denmark [online] Mar. 2007, <URL: http://www.cbs.dtu.dk/services/NetMHC/>, [retrieved on Jun. 6, 2013]. Retrieved from the Internet using the WayBack Machine <URL: http://web.archive.org/web/20071124222305/http://www.cbs.dtu.dk/services/NetMHC/>, 2 pages.
"The Immune Epitope Database and Analysis Resource (IEDB)" [online] Dec. 2007, <URL http://www.immuneepitope.org/home.do> Retrieved from the Internet using the Wayback Machine on Jun. 6, 2013, <URL http://web.archive.org/web/20071223055422/http://www.immuneepitope.org/home.do>, 1 page.
Artenstein and Grabenstein, "Smallpox Vaccines for Biodefense: Need and Feasibility," *Expert Rev. Vaccines*, 7(8):1225-1237, Oct. 2008.
Belyakov et al., "Mucosal Immunization with HIV-1 Peptide Vaccine Induces Mucosal and Systemic Cytotoxic T Lymphocytes and Protective Immunity in Mice Against Intrarectal Recombinant HIV-Vaccinia Challenge," *Proc. Natl. Acad. Sci. U.S.A.*, 95(4):1709-1714, Feb. 1998.
Buus et al., "Sensitive Quantitative Predictions of Peptide-MHC Binding by a 'Query by Committee' Artificial Neural Network Approach," *Tissue Antigens*, 62(5):378-384 Nov. 2003.
Di Giulio and Eckburg, "Human Monkeypox: an Emerging Zoonosis," *Lancet Infect. Dis.*, 4(1):15-25, Jan. 2004
Drexler et al., "Identification of Vaccinia Virus Epitope-Specific HLA-A*0201-Restricted T Cells and Comparative Analysis of Smallpox Vaccines," *Proc. Natl. Acad. Sci. U.S.A.*, 1001(1):217-222, Jan. 2003
Elias and Gygi, "Target-Decoy Search Strategy for Increased Confidence in Large-Scale Protein Identifications by Mass Spectrometry," *Nat. Methods*, 4(3):207-214, Mar. 2007.
Harndahl et al., "Real-Time, High-Throughput Measurements of Peptide—MHC-I Dissociation Using a Scintillation Proximity Assay," *J Immunol Methods.*, 3741-2:5-12, print Nov. 2011, online Oct. 2010.
Hogan et al., "Use of Selected Reaction Monitoring Mass Spectrometry for the Detection of Specific MHC Class I Peptide Antigens on A3 Supertype Family Members," *Cancer Immunol. Immunother.*, 54(4):359-371, print Apr. 2005, epub Sep. 2004.
Jackson et al., "A Totally Synthetic Vaccine of Generic Structure that Targets Toll-Like Receptor 2 on Dendritic Cells and Promotes Antibody or Cytotoxic T Cell Responses.," *Proc. Natl. Acad. Sci. U.S.A.*, 101(43):15440-15445, Oct. 2004.
Johnson et al., "Accurate Mass Precursor Ion Data and Tandem Mass Spectrometry Identify a Class I Human Leukocyte Antigen A*0201-Presented Peptide Originating from Vaccinia Virus," *J. Am. Soc. Mass Spectrom.*, 16(11):1812-1817, print Nov. 2005, epub Sep. 2005.
Johnson et al., "Discovery of Naturally Processed and HLA-Presented Class I Peptides from Vaccinia Virus Infection Using Mass Spectrometry for Vaccine Development," *Vaccine*, 281:38-47, print Dec. 2009, Epub Oct. 2009.
Keller et al., "Empirical Statistical Model to Estimate the Accuracy of Peptide Identifications Made by MS/MS and Database Search," *Anal. Chem.*, 74(20):5383-5392, Oct. 2002.

(Continued)

*Primary Examiner* — Nick Zou
(74) *Attorney, Agent, or Firm* — Fish & Richardson P.C.

(57) ABSTRACT

This document provides methods and materials related to polypeptides present in a vaccinia virus (e.g., polypeptides that can be isolated from naturally processed and presented class I polypeptides originating from vaccinia virus, a member of the Orthopoxvirus family). For example, methods for generating a vaccine comprising one or more of vaccinia virus polypeptides disclosed herein for preventing or treating Orthopoxvirus infection are provided. In addition, kits related to the use of vaccinia polypeptides are provided.

1 Claim, 5 Drawing Sheets

(56) References Cited

OTHER PUBLICATIONS

Kennedy and Poland, "T-Cell Epitope Discovery for Variola and Vaccinia Viruses," *Rev Med Virol*. 172:93-113, Mar.-Apr. 2007.
Lundegaard et al., "Accurate Approximation Method for Prediction of Class I MHC Affinities for Peptides of Length 8, 10 and 11 Using Prediction Tools Trained on 9mers," *Bioinformatics*, 24(11):1397-1398, print Jun. 2008, epub Apr. 2008.
Lundegaard et al., "NetMHC-3.0: Accurate Web Accessible Predictions of Human, Mouse and Monkey MHC Class I Affinities for Peptides of Length 8-11," *Nucl. Acids Res.*, 36(suppl 2): W509-W512, print Jul. 2008, epub May 2008.
Moutaftsi M et al. Correlates of Protection Efficacy Induced by Vaccinia Virus-Specific CD8+ T-Cell Epitopes in the Murine Intranasal Challenge Model. Eur J Immunol. Mar. 2009;39(3):717-722.
Neisig et al., "Reduced Cell Surface Expression of HLA-C Molecules Correlates with Restricted Peptide Binding and Stable TAP Interaction.," *J. Immunol.*, 160(1):171-179, Jan. 1998.
Nesvizhskii et al., "A Statistical Model for Identifying Proteins by Tandem Mass Spectrometry," *Anal. Chem.*, 75(17): 4646-4658, print Sep. 2003, epub Jul. 2003.
Nielsen et al., "Reliable Prediction of T-Cell Epitopes Using Neural Networks with Novel Sequence Representations," *Protein Sci.*, 12(5):1007-1017, May 2003.
Olsen et al., "Parts Per Million Mass Accuracy on an Orbitrap Mass Spectrometer Via Lock Mass Injection Into a C-Trap," *Mol. Cell Proteomics*, 4(12):2010-2021, print Dec. 2005, epub Oct. 2005.
Osborne et al., "Genomic Differences of Vaccinia Virus Clones from Dryvax Smallpox Vaccine: the Dryvax-Like ACAM2000 and the Mouse Neurovirulent Clone-3," *Vaccine*, 25(52):8807-8832, print Dec. 2007, epub Nov. 2007.
Ovsyannikova et al., "Discovery of Naturally Processed Class I HLA Vaccinia Virus T-Cell Epitopes Using Mass Spectrometry: Rational Design of a Multiepitope Smallpox Vaccine," The Eleventh Annual Conference on Vaccine Research, Baltimore, MD, May 5-7, 2008 p. 59, abstract S10, 2 pages.
Parham et al., "Use of a Monoclonal Antibody (W6/32) in Structural Studies of HLA-A,B,C, Antigens," *J. Immunol.*, 123(1):342-349, Jul. 1979.
Parker, et al., "Scheme for Ranking Potential HLA-A2 Binding Peptides Based on Independent Binding of Individual Peptide Side-Chains," *J. Immunol.*, 152(1):163-175, Jan. 1994.
Peters and Sette, "Integrating Epitope Data Into the Emerging Web of Biomedical Knowledge Resources," *Nat. Rev. Immunol.*, 7(6):485-490, Jun. 2007.
Rammensee et al, "SYFPEITHI: Database for MHC Ligands and Peptide Motifs," Immunogenetics, 50(3-4):213-219, Nov. 1999.
Rammensee et al., "MHC Ligands and Peptide Motifs: First Listing," *Immunogenetics*, 41(4):178-228, 1995.
Slingluff et al., "Recognition of Human Melanoma Cells by HLA-A2.1-Restricted Cytotoxic T Lymphocytes is Mediated by at Least Six Shared Peptide Epitopes," *J. Immunol.*, 150(7):2955-2963, Apr. 1993.
Snary et al., "Molecular Structure of Human Histocompatibility Antigens: the HLA-C Series," *Eur. J. Immunol.*, 7(8):580-585, Aug. 1977.
Snyder et al., "Protection Against Lethal Vaccinia Virus Challenge in HLA-A2 Transgenic Mice by Immunization with a Single CD8+ T-Cell Peptide Epitope of Vaccinia and Variola Viruses," *J. Virol.*, 78(13):7052-7060, Jul. 2004.
Vitalis et al., "Using the TAP Component of the Antigen-Processing Machinery as a Molecular Adjuvant," *PLoS Pathog.*, 1(4):e36, Dec. 2005.

\* cited by examiner

SEQUENCE LISTING

```
<160> NUMBER OF SEQ ID NOS: 116

<210> SEQ ID NO 1
<211> LENGTH: 9
<212> TYPE: PRT
<213> ORGANISM: Vaccinia virus

<400> SEQUENCE: 1

Ile Leu Ile Arg Gly Ile Ile Asn Val
1               5
```

```
<210> SEQ ID NO 2
<211> LENGTH: 12
<212> TYPE: PRT
<213> ORGANISM: Vaccinia virus

<400> SEQUENCE: 2

Ala Gln Ile Thr Thr Asp Asp Leu Val Lys Ser Tyr
1               5                   10

<210> SEQ ID NO 3
<211> LENGTH: 12
<212> TYPE: PRT
<213> ORGANISM: Vaccinia virus

<400> SEQUENCE: 3

Val Gln Ala Val Thr Asn Ala Gly Lys Ile Val Tyr
1               5                   10

<210> SEQ ID NO 4
<211> LENGTH: 12
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: Oxidized-Met

<400> SEQUENCE: 4

Ser Met Ala Asp Val Ser Ile Lys Thr Asn Ser Val
1               5                   10

<210> SEQ ID NO 5
<211> LENGTH: 11
<212> TYPE: PRT
<213> ORGANISM: Vaccinia virus

<400> SEQUENCE: 5

Leu Leu Phe Glu Asp Ile Ile Gln Asn Glu Tyr
1               5                   10

<210> SEQ ID NO 6
<211> LENGTH: 9
<212> TYPE: PRT
<213> ORGANISM: Vaccinia virus

<400> SEQUENCE: 6

Phe Thr Val Asn Ile Phe Lys Glu Val
1               5

<210> SEQ ID NO 7
<211> LENGTH: 16
<212> TYPE: PRT
<213> ORGANISM: Vaccinia virus

<400> SEQUENCE: 7

Gly Asp Lys Phe Thr Thr Arg Thr Ser Gln Lys Gly Thr Val Ala Tyr
1               5                   10                  15

<210> SEQ ID NO 8
<211> LENGTH: 11
<212> TYPE: PRT
<213> ORGANISM: Vaccinia virus

<400> SEQUENCE: 8

Ile Leu Tyr Asp Pro Glu Thr Asp Lys Pro Tyr
1               5                   10
```

```
<210> SEQ ID NO 9
<211> LENGTH: 12
<212> TYPE: PRT
<213> ORGANISM: Vaccinia virus

<400> SEQUENCE: 9

Thr Thr Arg Thr Ser Gln Lys Gly Thr Val Ala Tyr
1               5                   10

<210> SEQ ID NO 10
<211> LENGTH: 9
<212> TYPE: PRT
<213> ORGANISM: Vaccinia virus

<400> SEQUENCE: 10

Val Ile Ile Asn Ser Thr Ser Ile Phe
1               5

<210> SEQ ID NO 11
<211> LENGTH: 10
<212> TYPE: PRT
<213> ORGANISM: Vaccinia virus

<400> SEQUENCE: 11

Leu Thr Arg Glu Met Gly Phe Leu Val Tyr
1               5                   10

<210> SEQ ID NO 12
<211> LENGTH: 13
<212> TYPE: PRT
<213> ORGANISM: Vaccinia virus

<400> SEQUENCE: 12

Thr Val Ile Asn Glu Asp Ile Val Ser Lys Leu Thr Phe
1               5                   10

<210> SEQ ID NO 13
<211> LENGTH: 10
<212> TYPE: PRT
<213> ORGANISM: Vaccinia virus

<400> SEQUENCE: 13

Thr Leu Arg Phe Leu Glu Lys Thr Ser Phe
1               5                   10

<210> SEQ ID NO 14
<211> LENGTH: 10
<212> TYPE: PRT
<213> ORGANISM: Vaccinia virus

<400> SEQUENCE: 14

Val Gln Ile Asp Val Arg Asp Ile Lys Tyr
1               5                   10

<210> SEQ ID NO 15
<211> LENGTH: 9
<212> TYPE: PRT
<213> ORGANISM: Vaccinia virus

<400> SEQUENCE: 15

Tyr Ile Ile Gly Asn Ile Lys Thr Val
1               5
```

```
<210> SEQ ID NO 16
<211> LENGTH: 13
<212> TYPE: PRT
<213> ORGANISM: Vaccinia virus

<400> SEQUENCE: 16

Ile Gln Tyr Pro Gly Ser Glu Ile Lys Gly Asn Ala Tyr
1               5                   10

<210> SEQ ID NO 17
<211> LENGTH: 13
<212> TYPE: PRT
<213> ORGANISM: Vaccinia virus

<400> SEQUENCE: 17

Ile Gln Tyr Pro Gly Ser Lys Ile Lys Gly Asn Ala Tyr
1               5                   10

<210> SEQ ID NO 18
<211> LENGTH: 14
<212> TYPE: PRT
<213> ORGANISM: Vaccinia virus

<400> SEQUENCE: 18

Ile Gln Tyr Pro Gly Ser Lys Ile Lys Gly Asn Ala Tyr Phe
1               5                   10

<210> SEQ ID NO 19
<211> LENGTH: 9
<212> TYPE: PRT
<213> ORGANISM: Vaccinia virus

<400> SEQUENCE: 19

Lys Ile Ser Asn Thr Thr Phe Glu Val
1               5

<210> SEQ ID NO 20
<211> LENGTH: 13
<212> TYPE: PRT
<213> ORGANISM: Vaccinia virus

<400> SEQUENCE: 20

Leu Leu Ile Ser Ala Asp Asp Val Gln Glu Ile Arg Val
1               5                   10

<210> SEQ ID NO 21
<211> LENGTH: 12
<212> TYPE: PRT
<213> ORGANISM: Vaccinia virus

<400> SEQUENCE: 21

Thr Leu Tyr Asp Ile Ser Pro Gly His Val Tyr Ala
1               5                   10

<210> SEQ ID NO 22
<211> LENGTH: 11
<212> TYPE: PRT
<213> ORGANISM: Vaccinia virus

<400> SEQUENCE: 22

Tyr Pro Gly Ser Lys Ile Lys Gly Asn Ala Tyr
1               5                   10
```

<210> SEQ ID NO 23
<211> LENGTH: 11
<212> TYPE: PRT
<213> ORGANISM: Vaccinia virus

<400> SEQUENCE: 23

Val Ile Arg Asn Glu Val Asn Asp Thr His Tyr
1               5                   10

<210> SEQ ID NO 24
<211> LENGTH: 9
<212> TYPE: PRT
<213> ORGANISM: Vaccinia virus

<400> SEQUENCE: 24

Phe Gln Gln Lys Val Leu Gln Glu Tyr
1               5

<210> SEQ ID NO 25
<211> LENGTH: 11
<212> TYPE: PRT
<213> ORGANISM: Vaccinia virus

<400> SEQUENCE: 25

Val Ala Tyr Ala Ala Ala Lys Gly Ala Ser Met
1               5                   10

<210> SEQ ID NO 26
<211> LENGTH: 11
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: May or may not be oxidized-Met

<400> SEQUENCE: 26

Ile Met Asn Asn Pro Asp Phe Lys Thr Thr Tyr
1               5                   10

<210> SEQ ID NO 27
<211> LENGTH: 12
<212> TYPE: PRT
<213> ORGANISM: Vaccinia virus

<400> SEQUENCE: 27

Val Gln Lys Gln Asp Ile Val Lys Leu Thr Val Tyr
1               5                   10

<210> SEQ ID NO 28
<211> LENGTH: 11
<212> TYPE: PRT
<213> ORGANISM: Vaccinia virus

<400> SEQUENCE: 28

Lys Leu Phe Asn Glu Asp Leu Ser Ser Lys Tyr
1               5                   10

<210> SEQ ID NO 29
<211> LENGTH: 9
<212> TYPE: PRT
<213> ORGANISM: Vaccinia virus

<400> SEQUENCE: 29

Leu Ile Gln Glu Ile Val His Glu Val
1               5

```
<210> SEQ ID NO 30
<211> LENGTH: 9
<212> TYPE: PRT
<213> ORGANISM: Vaccinia virus

<400> SEQUENCE: 30

Leu Val Ile Glu Asn Asp Ser Gln Phe
1               5

<210> SEQ ID NO 31
<211> LENGTH: 12
<212> TYPE: PRT
<213> ORGANISM: Vaccinia virus

<400> SEQUENCE: 31

Lys Leu Tyr Lys Ser Gly Asn Ser His Ile Asp Tyr
1               5                   10

<210> SEQ ID NO 32
<211> LENGTH: 12
<212> TYPE: PRT
<213> ORGANISM: Vaccinia virus

<400> SEQUENCE: 32

Arg Val Phe Ala Pro Lys Asp Thr Glu Ser Val Phe
1               5                   10

<210> SEQ ID NO 33
<211> LENGTH: 9
<212> TYPE: PRT
<213> ORGANISM: Vaccinia virus

<400> SEQUENCE: 33

Lys Val Ser Ala Gln Asn Ile Ser Phe
1               5

<210> SEQ ID NO 34
<211> LENGTH: 10
<212> TYPE: PRT
<213> ORGANISM: Vaccinia virus

<400> SEQUENCE: 34

Gly Gln Leu Tyr Ser Thr Leu Leu Ser Phe
1               5                   10

<210> SEQ ID NO 35
<211> LENGTH: 11
<212> TYPE: PRT
<213> ORGANISM: Vaccinia virus

<400> SEQUENCE: 35

Leu Gln Tyr Ala Pro Arg Glu Leu Leu Gln Tyr
1               5                   10

<210> SEQ ID NO 36
<211> LENGTH: 11
<212> TYPE: PRT
<213> ORGANISM: Vaccinia virus
<220> FEATURE:
<221> NAME/KEY: MOD_RES
<222> LOCATION: (5)..(5)
<223> OTHER INFORMATION: Oxidized-Met

<400> SEQUENCE: 36

His Cys Tyr Leu Met Asn Glu Gly Phe Glu Ser
1               5                   10
```

```
<210> SEQ ID NO 37
<211> LENGTH: 9
<212> TYPE: PRT
<213> ORGANISM: Vaccinia virus
<220> FEATURE:
<221> NAME/KEY: MOD_RES
<222> LOCATION: (1)..(1)
<223> OTHER INFORMATION: May or may not be oxidized-Met
<220> FEATURE:
<221> NAME/KEY: MOD_RES
<222> LOCATION: (7)..(7)
<223> OTHER INFORMATION: May or may not be oxidized-Met

<400> SEQUENCE: 37

Met Leu Ile Asn Tyr Leu Met Leu Leu
1               5

<210> SEQ ID NO 38
<211> LENGTH: 11
<212> TYPE: PRT
<213> ORGANISM: Vaccinia virus

<400> SEQUENCE: 38

Lys Ile Lys Asp Asp Phe Gln Thr Val Asn Phe
1               5                   10

<210> SEQ ID NO 39
<211> LENGTH: 10
<212> TYPE: PRT
<213> ORGANISM: Vaccinia virus

<400> SEQUENCE: 39

Lys Ile Tyr Gly Ser Asp Ser Ile Glu Phe
1               5                   10

<210> SEQ ID NO 40
<211> LENGTH: 10
<212> TYPE: PRT
<213> ORGANISM: Vaccinia virus
<220> FEATURE:
<221> NAME/KEY: MOD_RES
<222> LOCATION: (3)..(3)
<223> OTHER INFORMATION: Oxidized-Met

<400> SEQUENCE: 40

Tyr Val Met Gly Gly Val Tyr Thr Thr Tyr
1               5                   10

<210> SEQ ID NO 41
<211> LENGTH: 9
<212> TYPE: PRT
<213> ORGANISM: Vaccinia virus

<400> SEQUENCE: 41

Lys Leu Ser Asp Ser Lys Ile Thr Val
1               5

<210> SEQ ID NO 42
<211> LENGTH: 9
<212> TYPE: PRT
<213> ORGANISM: Vaccinia virus

<400> SEQUENCE: 42

Val Leu Ser Leu Glu Leu Pro Glu Val
1               5
```

```
<210> SEQ ID NO 43
<211> LENGTH: 11
<212> TYPE: PRT
<213> ORGANISM: Vaccinia virus

<400> SEQUENCE: 43

Ile Leu Val Pro Asn Ile Asn Ile Leu Lys Ile
1               5                   10

<210> SEQ ID NO 44
<211> LENGTH: 11
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: Oxidized-Met

<400> SEQUENCE: 44

Ile Met Ser Glu Ser Tyr Thr Leu Lys Glu Val
1               5                   10

<210> SEQ ID NO 45
<211> LENGTH: 9
<212> TYPE: PRT
<213> ORGANISM: Vaccinia virus

<400> SEQUENCE: 45

Arg Leu Lys Pro Leu Asp Ile His Tyr
1               5

<210> SEQ ID NO 46
<211> LENGTH: 11
<212> TYPE: PRT
<213> ORGANISM: Vaccinia virus

<400> SEQUENCE: 46

Tyr Ala Ile Asp Val Ser Lys Val Lys Pro Leu
1               5                   10

<210> SEQ ID NO 47
<211> LENGTH: 12
<212> TYPE: PRT
<213> ORGANISM: Vaccinia virus
<220> FEATURE:
<221> NAME/KEY: MOD_RES
<222> LOCATION: (10)..(10)
<223> OTHER INFORMATION: Oxidized-Met

<400> SEQUENCE: 47

Gly Lys Ala Ser Gln Asn Pro Ser Lys Met Val Tyr
1               5                   10

<210> SEQ ID NO 48
<211> LENGTH: 13
<212> TYPE: PRT
<213> ORGANISM: Vaccinia virus
<220> FEATURE:
<221> NAME/KEY: MOD_RES
<222> LOCATION: (11)..(11)
<223> OTHER INFORMATION: Oxidized-Met

<400> SEQUENCE: 48

Ile Gly Lys Ala Ser Gln Asn Pro Ser Lys Met Val Tyr
1               5                   10
```

```
<210> SEQ ID NO 49
<211> LENGTH: 9
<212> TYPE: PRT
<213> ORGANISM: Vaccinia virus

<400> SEQUENCE: 49

Lys Leu Phe Ser Asp Ile Ser Ala Ile
1               5

<210> SEQ ID NO 50
<211> LENGTH: 9
<212> TYPE: PRT
<213> ORGANISM: Vaccinia virus
<220> FEATURE:
<221> NAME/KEY: MOD_RES
<222> LOCATION: (7)..(7)
<223> OTHER INFORMATION: Oxidized-Met

<400> SEQUENCE: 50

Ser Gln Asn Pro Ser Lys Met Val Tyr
1               5

<210> SEQ ID NO 51
<211> LENGTH: 8
<212> TYPE: PRT
<213> ORGANISM: Vaccinia virus

<400> SEQUENCE: 51

Leu Ala Arg Leu Gly Leu Val Leu
1               5

<210> SEQ ID NO 52
<211> LENGTH: 10
<212> TYPE: PRT
<213> ORGANISM: Vaccinia virus

<400> SEQUENCE: 52

Gly Ser Phe Ser Gly Arg Tyr Val Ser Tyr
1               5                   10

<210> SEQ ID NO 53
<211> LENGTH: 12
<212> TYPE: PRT
<213> ORGANISM: Vaccinia virus

<400> SEQUENCE: 53

Lys Gln Lys Phe Pro Tyr Glu Gly Gly Lys Val Phe
1               5                   10

<210> SEQ ID NO 54
<211> LENGTH: 11
<212> TYPE: PRT
<213> ORGANISM: Vaccinia virus

<400> SEQUENCE: 54

Ile Gln His Arg Gln Gln Leu Glu Leu Ala Tyr
1               5                   10

<210> SEQ ID NO 55
<211> LENGTH: 9
<212> TYPE: PRT
<213> ORGANISM: Vaccinia virus

<400> SEQUENCE: 55

Ile Gln Lys Asp Ile Asn Ile Thr His
1               5
```

```
<210> SEQ ID NO 56
<211> LENGTH: 9
<212> TYPE: PRT
<213> ORGANISM: Vaccinia virus

<400> SEQUENCE: 56

Met Leu Thr Glu Phe Leu His Tyr Cys
1               5

<210> SEQ ID NO 57
<211> LENGTH: 11
<212> TYPE: PRT
<213> ORGANISM: Vaccinia virus
<220> FEATURE:
<221> NAME/KEY: MOD_RES
<222> LOCATION: (3)..(3)
<223> OTHER INFORMATION: May or may not be oxidized-Met

<400> SEQUENCE: 57

Leu Phe Met Asp Glu Ile Asp His Glu Ser Tyr
1               5                   10

<210> SEQ ID NO 58
<211> LENGTH: 11
<212> TYPE: PRT
<213> ORGANISM: Vaccinia virus

<400> SEQUENCE: 58

Val Gln Ile Leu Met Lys Thr Ala Asn Asn Tyr
1               5                   10

<210> SEQ ID NO 59
<211> LENGTH: 11
<212> TYPE: PRT
<213> ORGANISM: Vaccinia virus

<400> SEQUENCE: 59

Lys Gln Ile Ser Ile Ser Thr Gly Val Leu Tyr
1               5                   10

<210> SEQ ID NO 60
<211> LENGTH: 13
<212> TYPE: PRT
<213> ORGANISM: Vaccinia virus

<400> SEQUENCE: 60

Arg Val Lys Gln Ile Ser Ile Ser Thr Gly Val Leu Tyr
1               5                   10

<210> SEQ ID NO 61
<211> LENGTH: 12
<212> TYPE: PRT
<213> ORGANISM: Vaccinia virus
<220> FEATURE:
<221> NAME/KEY: MOD_RES
<222> LOCATION: (3)..(3)
<223> OTHER INFORMATION: Oxidized-Met

<400> SEQUENCE: 61

Ile Leu Met Asp Asn Lys Gly Leu Gly Val Arg Leu
1               5                   10

<210> SEQ ID NO 62
<211> LENGTH: 10
<212> TYPE: PRT
<213> ORGANISM: Vaccinia virus
```

```
<400> SEQUENCE: 62

Arg Gln Leu Pro Thr Lys Thr Arg Ser Tyr
1               5                   10

<210> SEQ ID NO 63
<211> LENGTH: 11
<212> TYPE: PRT
<213> ORGANISM: Vaccinia virus

<400> SEQUENCE: 63

Ile Leu Lys Ser Glu Ile Glu Lys Ala Thr Tyr
1               5                   10

<210> SEQ ID NO 64
<211> LENGTH: 9
<212> TYPE: PRT
<213> ORGANISM: Vaccinia virus

<400> SEQUENCE: 64

Ile Leu Ile Glu Ile Ile Pro Lys Ile
1               5

<210> SEQ ID NO 65
<211> LENGTH: 10
<212> TYPE: PRT
<213> ORGANISM: Vaccinia virus

<400> SEQUENCE: 65

Ile Thr Asn Lys Ala Asp Thr Ser Ser Phe
1               5                   10

<210> SEQ ID NO 66
<211> LENGTH: 9
<212> TYPE: PRT
<213> ORGANISM: Vaccinia virus

<400> SEQUENCE: 66

Ile Ile Lys Glu Asp Ile Ser Glu Tyr
1               5

<210> SEQ ID NO 67
<211> LENGTH: 9
<212> TYPE: PRT
<213> ORGANISM: Vaccinia virus

<400> SEQUENCE: 67

Tyr Ser Lys Lys Phe Gln Glu Ser Phe
1               5

<210> SEQ ID NO 68
<211> LENGTH: 10
<212> TYPE: PRT
<213> ORGANISM: Vaccinia virus

<400> SEQUENCE: 68

Lys Leu Leu Leu Gly Glu Leu Phe Phe Leu
1               5                   10

<210> SEQ ID NO 69
<211> LENGTH: 12
<212> TYPE: PRT
<213> ORGANISM: Vaccinia virus
```

```
<400> SEQUENCE: 69

Leu Gln Lys Gly His Asn Lys Phe Pro Val Asn Phe
1               5                   10

<210> SEQ ID NO 70
<211> LENGTH: 10
<212> TYPE: PRT
<213> ORGANISM: Vaccinia virus

<400> SEQUENCE: 70

Val Val Ile Gly Asn Thr Leu Ile Lys Tyr
1               5                   10

<210> SEQ ID NO 71
<211> LENGTH: 10
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: Oxidized-Met

<400> SEQUENCE: 71

Lys Met Ile Ile Glu Lys His Val Glu Tyr
1               5                   10

<210> SEQ ID NO 72
<211> LENGTH: 9
<212> TYPE: PRT
<213> ORGANISM: Vaccinia virus
<220> FEATURE:
<221> NAME/KEY: MOD_RES
<222> LOCATION: (1)..(1)
<223> OTHER INFORMATION: Oxidized-Met

<400> SEQUENCE: 72

Met Ile Ile Glu Lys His Val Glu Tyr
1               5

<210> SEQ ID NO 73
<211> LENGTH: 10
<212> TYPE: PRT
<213> ORGANISM: Vaccinia virus

<400> SEQUENCE: 73

Ser Leu Leu Phe Ile Pro Asp Ile Lys Leu
1               5                   10

<210> SEQ ID NO 74
<211> LENGTH: 12
<212> TYPE: PRT
<213> ORGANISM: Vaccinia virus

<400> SEQUENCE: 74

Ser Gln Phe Asp Asp Lys Gly Asn Thr Ala Leu Tyr
1               5                   10

<210> SEQ ID NO 75
<211> LENGTH: 11
<212> TYPE: PRT
<213> ORGANISM: Vaccinia virus
<220> FEATURE:
<221> NAME/KEY: MOD_RES
<222> LOCATION: (11)..(11)
<223> OTHER INFORMATION: Oxidized-Met
```

-continued

```
<400> SEQUENCE: 75

Val Leu Leu Asp Asp Ala Glu Ile Ala Lys Met
1               5                   10

<210> SEQ ID NO 76
<211> LENGTH: 13
<212> TYPE: PRT
<213> ORGANISM: Vaccinia virus
<220> FEATURE:
<221> NAME/KEY: MOD_RES
<222> LOCATION: (11)..(11)
<223> OTHER INFORMATION: May or may not be oxidized-Met

<400> SEQUENCE: 76

Val Leu Leu Asp Asp Ala Glu Ile Ala Lys Met Ile Ile
1               5                   10

<210> SEQ ID NO 77
<211> LENGTH: 9
<212> TYPE: PRT
<213> ORGANISM: Vaccinia virus

<400> SEQUENCE: 77

Lys Leu Val Gly Lys Thr Val Lys Val
1               5

<210> SEQ ID NO 78
<211> LENGTH: 9
<212> TYPE: PRT
<213> ORGANISM: Vaccinia virus

<400> SEQUENCE: 78

Ile Thr Tyr Pro Lys Ala Leu Val Phe
1               5

<210> SEQ ID NO 79
<211> LENGTH: 13
<212> TYPE: PRT
<213> ORGANISM: Vaccinia virus

<400> SEQUENCE: 79

Met Met Ile Asp Asp Phe Gly Thr Ala Arg Gly Asn Tyr
1               5                   10

<210> SEQ ID NO 80
<211> LENGTH: 11
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: Oxidized-Met

<400> SEQUENCE: 80

Leu Met Lys Phe Asp Asp Val Ala Ile Arg Tyr
1               5                   10

<210> SEQ ID NO 81
<211> LENGTH: 9
<212> TYPE: PRT
<213> ORGANISM: Vaccinia virus
<220> FEATURE:
<221> NAME/KEY: MOD_RES
<222> LOCATION: (7)..(7)
<223> OTHER INFORMATION: May or may not be oxidized-Met
```

```
<400> SEQUENCE: 81

Arg Leu Tyr Lys Glu Leu Met Lys Phe
1               5

<210> SEQ ID NO 82
<211> LENGTH: 9
<212> TYPE: PRT
<213> ORGANISM: Vaccinia virus

<400> SEQUENCE: 82

His Ile Ile Lys Glu Phe Met Thr Tyr
1               5

<210> SEQ ID NO 83
<211> LENGTH: 9
<212> TYPE: PRT
<213> ORGANISM: Vaccinia virus

<400> SEQUENCE: 83

Ser Ile Ile Ala Ile Leu Asp Arg Phe
1               5

<210> SEQ ID NO 84
<211> LENGTH: 9
<212> TYPE: PRT
<213> ORGANISM: Vaccinia virus

<400> SEQUENCE: 84

Gly Leu Leu Asp Arg Leu Tyr Asp Leu
1               5

<210> SEQ ID NO 85
<211> LENGTH: 9
<212> TYPE: PRT
<213> ORGANISM: Vaccinia virus

<400> SEQUENCE: 85

Ile Val Ile Glu Ala Ile His Thr Val
1               5

<210> SEQ ID NO 86
<211> LENGTH: 9
<212> TYPE: PRT
<213> ORGANISM: Vaccinia virus

<400> SEQUENCE: 86

Ile Leu Ser Asp Glu Asn Tyr Leu Leu
1               5

<210> SEQ ID NO 87
<211> LENGTH: 9
<212> TYPE: PRT
<213> ORGANISM: Vaccinia virus

<400> SEQUENCE: 87

Ile Leu Asp Asp Asn Leu Tyr Lys Val
1               5

<210> SEQ ID NO 88
<211> LENGTH: 9
<212> TYPE: PRT
<213> ORGANISM: Vaccinia virus
```

```
<400> SEQUENCE: 88

Lys Leu Phe Thr His Asp Ile Met Leu
1               5

<210> SEQ ID NO 89
<211> LENGTH: 9
<212> TYPE: PRT
<213> ORGANISM: Vaccinia virus

<400> SEQUENCE: 89

Lys Ile Asp Tyr Tyr Ile Pro Tyr Val
1               5

<210> SEQ ID NO 90
<211> LENGTH: 9
<212> TYPE: PRT
<213> ORGANISM: Vaccinia virus

<400> SEQUENCE: 90

Phe Leu Thr Ser Val Ile Asn Arg Val
1               5

<210> SEQ ID NO 91
<211> LENGTH: 10
<212> TYPE: PRT
<213> ORGANISM: Vaccinia virus

<400> SEQUENCE: 91

Asn Leu Phe Asp Ile Pro Leu Leu Thr Val
1               5                   10

<210> SEQ ID NO 92
<211> LENGTH: 9
<212> TYPE: PRT
<213> ORGANISM: Vaccinia virus
<220> FEATURE:
<221> NAME/KEY: MOD_RES
<222> LOCATION: (1)..(1)
<223> OTHER INFORMATION: May or may not be oxidized-Met

<400> SEQUENCE: 92

Met Gln Lys Phe Thr Ile Leu Glu Tyr
1               5

<210> SEQ ID NO 93
<211> LENGTH: 9
<212> TYPE: PRT
<213> ORGANISM: Vaccinia virus

<400> SEQUENCE: 93

Ser Gln Ile Phe Asn Ile Ile Ser Tyr
1               5

<210> SEQ ID NO 94
<211> LENGTH: 9
<212> TYPE: PRT
<213> ORGANISM: Vaccinia virus

<400> SEQUENCE: 94

Ala Leu Asp Glu Lys Leu Phe Leu Ile
1               5
```

```
<210> SEQ ID NO 95
<211> LENGTH: 9
<212> TYPE: PRT
<213> ORGANISM: Vaccinia virus

<400> SEQUENCE: 95

His Met Ile Asp Lys Leu Phe Tyr Val
1               5

<210> SEQ ID NO 96
<211> LENGTH: 9
<212> TYPE: PRT
<213> ORGANISM: Vaccinia virus

<400> SEQUENCE: 96

Gln Ile Asp Val Arg Asp Ile Lys Tyr
1               5

<210> SEQ ID NO 97
<211> LENGTH: 10
<212> TYPE: PRT
<213> ORGANISM: Vaccinia virus

<400> SEQUENCE: 97

Ser Ile Met Asp Phe Ile Gly Pro Tyr Ile
1               5                   10

<210> SEQ ID NO 98
<211> LENGTH: 9
<212> TYPE: PRT
<213> ORGANISM: Vaccinia virus

<400> SEQUENCE: 98

Tyr Ala Ala Ala Lys Gly Ala Ser Met
1               5

<210> SEQ ID NO 99
<211> LENGTH: 9
<212> TYPE: PRT
<213> ORGANISM: Vaccinia virus

<400> SEQUENCE: 99

Ile Leu Gln Asn Arg Leu Val Tyr Val
1               5

<210> SEQ ID NO 100
<211> LENGTH: 9
<212> TYPE: PRT
<213> ORGANISM: Vaccinia virus

<400> SEQUENCE: 100

Ile Gln Phe Met His Glu Gln Gly Tyr
1               5

<210> SEQ ID NO 101
<211> LENGTH: 9
<212> TYPE: PRT
<213> ORGANISM: Vaccinia virus

<400> SEQUENCE: 101

Thr Leu Leu Asp His Ile Arg Thr Ala
1               5
```

```
<210> SEQ ID NO 102
<211> LENGTH: 9
<212> TYPE: PRT
<213> ORGANISM: Vaccinia virus

<400> SEQUENCE: 102

Arg Gln Phe Tyr Asn Ala Asn Val Leu
1               5

<210> SEQ ID NO 103
<211> LENGTH: 9
<212> TYPE: PRT
<213> ORGANISM: Vaccinia virus

<400> SEQUENCE: 103

Ile Leu Lys Ile Asn Ser Val Lys Tyr
1               5

<210> SEQ ID NO 104
<211> LENGTH: 10
<212> TYPE: PRT
<213> ORGANISM: Vaccinia virus

<400> SEQUENCE: 104

Leu Leu Leu Glu Thr Lys Thr Ile Leu Val
1               5                   10

<210> SEQ ID NO 105
<211> LENGTH: 9
<212> TYPE: PRT
<213> ORGANISM: Vaccinia virus

<400> SEQUENCE: 105

Ser Leu Ser Asn Leu Asp Phe Arg Leu
1               5

<210> SEQ ID NO 106
<211> LENGTH: 10
<212> TYPE: PRT
<213> ORGANISM: Vaccinia virus
<220> FEATURE:
<221> NAME/KEY: MOD_RES
<222> LOCATION: (3)..(3)
<223> OTHER INFORMATION: Oxidized-Met

<400> SEQUENCE: 106

Ile Leu Met Asp Asn Lys Gly Leu Gly Val
1               5                   10

<210> SEQ ID NO 107
<211> LENGTH: 9
<212> TYPE: PRT
<213> ORGANISM: Vaccinia virus

<400> SEQUENCE: 107

Gln Leu Ile Tyr Gln Arg Ile Tyr Tyr
1               5

<210> SEQ ID NO 108
<211> LENGTH: 9
<212> TYPE: PRT
<213> ORGANISM: Vaccinia virus

<400> SEQUENCE: 108

Ser Leu Lys Asp Val Leu Val Ser Val
1               5
```

```
<210> SEQ ID NO 109
<211> LENGTH: 9
<212> TYPE: PRT
<213> ORGANISM: Vaccinia virus
<220> FEATURE:
<221> NAME/KEY: MOD_RES
<222> LOCATION: (8)..(8)
<223> OTHER INFORMATION: Oxidized-Met

<400> SEQUENCE: 109

Val Pro Leu Pro Cys Gln Leu Met Tyr
1               5

<210> SEQ ID NO 110
<211> LENGTH: 9
<212> TYPE: PRT
<213> ORGANISM: Vaccinia virus

<400> SEQUENCE: 110

Asn Thr Ile Asp Lys Ser Ser Pro Leu
1               5

<210> SEQ ID NO 111
<211> LENGTH: 10
<212> TYPE: PRT
<213> ORGANISM: Vaccinia virus

<400> SEQUENCE: 111

Thr Gln Phe Asn Phe Asn Gly His Thr Tyr
1               5                   10

<210> SEQ ID NO 112
<211> LENGTH: 9
<212> TYPE: PRT
<213> ORGANISM: Vaccinia virus
<220> FEATURE:
<221> NAME/KEY: MOD_RES
<222> LOCATION: (2)..(2)
<223> OTHER INFORMATION: May or may not be oxidized-Met

<400> SEQUENCE: 112

Tyr Met Ile Glu Arg Phe Ile Ser Phe
1               5

<210> SEQ ID NO 113
<211> LENGTH: 10
<212> TYPE: PRT
<213> ORGANISM: Vaccinia virus

<400> SEQUENCE: 113

Tyr Leu Phe Asp Tyr Pro His Phe Glu Ala
1               5                   10

<210> SEQ ID NO 114
<211> LENGTH: 9
<212> TYPE: PRT
<213> ORGANISM: Vaccinia virus

<400> SEQUENCE: 114

Ile Ile Asn Asp Lys Gly Lys Gln Tyr
1               5

<210> SEQ ID NO 115
<211> LENGTH: 10
<212> TYPE: PRT
<213> ORGANISM: Vaccinia virus
```

-continued

```
<400> SEQUENCE: 115

Gln Ala Ile Glu Pro Ser Gly Asn Asn Tyr
1               5                   10

<210> SEQ ID NO 116
<211> LENGTH: 9
<212> TYPE: PRT
<213> ORGANISM: Vaccinia virus

<400> SEQUENCE: 116

Ile Leu Phe Arg Met Ile Glu Thr Tyr
1               5
```

US 9,389,232 B2

VACCINIA VIRUS POLYPEPTIDES

CROSS-REFERENCE TO RELATED APPLICATIONS

This application is a continuation of U.S. application Ser. No. 13/222,862, filed Aug. 31, 2011, which claims the benefit of U.S. Provisional Application Ser. No. 61/379,311, filed Sep. 1, 2010. The disclosure of the prior applications are considered part of (and are incorporated by reference in) the disclosure of this application.

BACKGROUND

1. Technical Field

This document provides methods and materials relating to isolated vaccinia virus-derived polypeptides. For example, this document relates to specific and naturally processed and HLA presented vaccinia virus-derived polypeptides isolated from vaccinia virus, a member of the Orthopoxvirus family. This document provides methods for generating a vaccine for preventing or treating Orthopoxvirus infection that induces a protective therapeutic immune response. The vaccines can include one or more of the isolated vaccinia virus polypeptides provided herein. In addition, this document provides kits related to the use of vaccinia virus polypeptides.

2. Background Information

Polypeptide-based vaccines use small polypeptide sequences derived from target proteins as epitopes to provoke an immune reaction. These vaccines are a result of an improved understanding of the molecular basis of epitope recognition, thereby permitting the development of rationally designed, epitope-specific vaccines based on motifs demonstrated to bind to human class I (HLA I) or class II (HLA II) major histocompatibility complex (MHC) molecules. Of particular interest has been the discovery of epitopes that are specifically recognized by T cells for prophylaxis and treatment of infectious diseases.

Over the centuries, naturally occurring smallpox, with its case-fatality rate of 30 percent or more and its ability to spread in any climate and season, has been universally feared as one of the most devastating of all the infectious diseases. The use of vaccinia virus as a vaccine enabled the global eradication of naturally occurring smallpox. The last naturally occurring case of smallpox occurred in Somalia in 1977. In May 1980, the World Health Assembly certified that the world was free of naturally occurring smallpox. Routine vaccination against smallpox in the United States ended in 1971, and except for some soldiers and laboratory workers, no one has been vaccinated since 1983. However, terrorist activities in the early 21st century as well as imported outbreaks of monkeypox (a member of the Orthopox virus family) in the USA, spurred renewed interest in biodefense countermeasures for these public health threats (Artenstein et al., *Expert Rev. Vaccines*, 7:1225-1237 (2008) and Giulio et al., *Lancet Infect. Dis.*, 4:15-25 (2004)).

SUMMARY

This document provides methods and materials related to vaccinia virus polypeptides. For example, this document provides vaccinia virus polypeptides that have the ability to be naturally processed and presented by HLA molecules. This document also provides methods and materials (e.g., vaccines) for preventing or treating Orthopoxvirus infections. For example, the vaccines provided herein can include one or more of the vaccinia virus polypeptides provided herein and can have the ability to induce a protective therapeutic immune response within a mammal (e.g., a human). In addition, this document provides kits related to the use of vaccinia virus polypeptides.

As described herein, two-dimensional liquid chromatography coupled to mass spectrometry was used to identify 116 vaccinia virus polypeptides, encoded by 61 open reading frames, from a human B-cell line (homozygous for HLA class I A*0201, B*1501, and C*03) after infection with vaccinia virus (Dryvax). The identification of these naturally processed and presented polypeptides resulting from vaccinia virus infection can be used to aid in understanding the immune process and can be used to generate vaccines against Orthopoxviruses.

In general, one aspect of this document features an isolated polypeptide, wherein the amino acid sequence of the polypeptide is as set forth in any one of SEQ ID NOs:1-83.

In another aspect, this document features a composition comprising at least one isolated polypeptide selected from the group consisting of SEQ ID NOs:1-82 and 83 and at least one polypeptide selected from the group consisting of SEQ ID NOs:84-115 and 116. The composition can further comprise an adjuvant.

In another aspect, this document features a method of preventing or treating variola virus infection in a subject. The method comprises, or consists essentially of, administering to the subject a composition comprising an adjuvant and at least one polypeptide, wherein the amino acid sequence of the polypeptide is as set forth in any one of SEQ ID NOs:1-83. The subject can be a human.

In another aspect, this document features a vaccine comprising, or consisting essentially of, at least one isolated polypeptide, wherein the amino acid sequence of the polypeptide is as set forth in any one of SEQ ID NOs:1-83. The vaccine can comprise at least one polypeptide selected from the group consisting of SEQ ID NOs:84-115 and 116. The vaccine can comprise an adjuvant.

In another aspect, this document features a method of enhancing the immune response in a subject to a vaccine. The method comprises, or consists essentially of, administering an agent capable of increasing the expression of a transporter associated with antigen processing in the subject, wherein the vaccine comprises at least one isolated polypeptide, wherein the amino acid sequence of the polypeptide is as set forth in any one of SEQ ID NOs:1-83. The transporter can be TAP1, TAP2, or Tapasin.

In another aspect, this document features a method of inducing an immune response against at least one isolated polypeptide selected from the group consisting of SEQ ID NOs:1-82 and 83. The method comprises, or consists essentially of, administering the polypeptide to a subject in an amount effective to induce an immune response against the polypeptide. The polypeptide can be administered in combination with a polypeptide selected from the group consisting of SEQ ID NOs: 84-115 and 116. The polypeptide can be administered in combination with a pharmaceutically acceptable excipient, carrier, diluent, or vehicle. The method can comprise administering to the subject an agent capable of increasing expression of a TAP molecule. The immune response can be a cell mediated immune response. The cell mediated immune response can be a cell mediated cytolytic immune response. The cell mediated immune response can be a class I-restricted T cell response.

In another aspect, this document features a kit comprising, or consisting essentially of, (a) at least one polypeptide selected from the group consisting of SEQ ID NOs:1-82 and 83, and (b) an adjuvant. The kit can comprise at least two polypeptides selected from the group. The kit can comprise at least one polypeptide selected from the group consisting of SEQ ID NOs:84-115 and 116.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
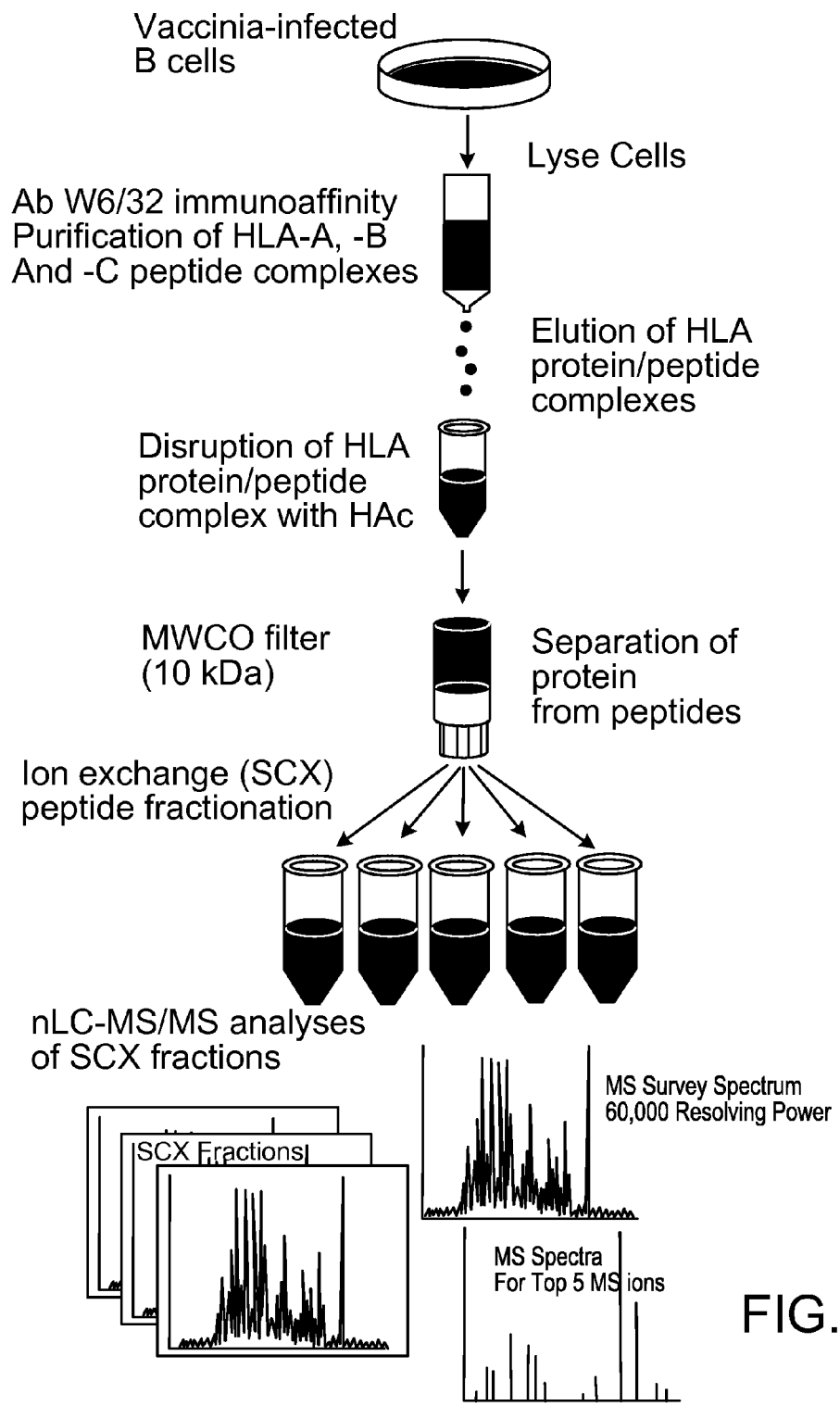
FIG. 1 is a diagram of a protocol for isolating and identifying HLA class I polypeptides from B cells infected with vaccinia virus.

This document provides methods and materials related to vaccinia virus polypeptides. For example, this document provides vaccinia virus polypeptides that have the ability to be naturally processed and presented by HLA molecules. This document also provides methods and materials (e.g., vaccines) for preventing or treating Orthopoxvirus infections. For example, the vaccines provided herein can include one or more of the vaccinia virus polypeptides provided herein and can have the ability to induce a protective therapeutic immune response within a mammal (e.g., a human). In addition, this document provides kits related to the use of vaccinia virus polypeptides.

This document provides compositions (e.g., vaccine compositions) containing one or more vaccinia virus polypeptides provided herein. In some cases, a vaccinia virus polypeptide provided herein can have the ability to be naturally processed and presented by a class I MHC molecule. Examples of such vaccinia virus polypeptide provided herein include, without limitation, those vaccinia virus polypeptides set forth in SEQ ID NOs:1-83 of Table 2. In some cases, the polypeptides set forth in SEQ ID NOs:1-83 can be used individually or as a mixture for the prevention and/or therapeutic treatment of Orthopoxvirus infections in vitro and in vivo, and/or for improved diagnostic detection of Orthopoxvirus infections. Any appropriate combination of the polypeptides listed in Table 2 can be used. For example, the combination can include at least 2, 3, 5, 10, 15, 20, 25, 30, 35, 40, 45, 50, or more polypeptides selected from Table 2. For example, the polypeptides corresponding to SEQ ID NOs: 1-10 can be used in any combination. In some cases, the polypeptides corresponding to SEQ ID NOs:1-10 and SEQ ID NOs:70-83 can be used in any combination. For example, the polypeptides corresponding to SEQ ID NO:1 and SEQ ID NO:3 can be used in any combination with SEQ ID NOs:70-83. In some cases, a combination of the polypeptides listed in Table 2 can be used with the exception of 2, 3, 5, 10, 15, 20, 25, 30, 35, 40, 45, 50, or more polypeptides selected from Table 2. For example, the polypeptides corresponding to SEQ ID NOs:1-10 can be used in any combination with the exception of SEQ ID NOs:11-83. For example, the polypeptides corresponding to SEQ ID NOs:1-83 can be used in any combination with the exception of SEQ ID NO:10, SEQ ID NO:20 and SEQ ID NO:30.

In some cases, one or more of the polypeptides set forth in SEQ ID NOs:1-83 can be used in combination with at least one of the polypeptides set forth in SEQ ID NOs:84-116 of Table 3. Any appropriate combination of the polypeptides listed in Table 2 can be used with at least one of the polypeptides set forth in SEQ ID NOs:84-116 of Table 3. In some cases, a combination can include at least 2, 3, 5, 10, 15, 20, 25, 30, 35, 40, 45, 50, or more polypeptides selected from Table 2 with at least one of the polypeptides set forth in Table 3. For example, the polypeptides corresponding to SEQ ID NOs:1-10 from Table 2 can be used in combination with SEQ ID NO:84 of Table 3. In some cases, the polypeptides corresponding to SEQ ID NOs:1-10 and SEQ ID NOs:70-83 can be used in combination with SEQ ID NO:84. In some cases, the combination can include at least 2, 3, 5, 10, 15, 20, 25, 30, 35, 40, 45, 50, or more polypeptides selected from Table 2 with at least 2, 3, 5, 10, 15, 20, 25, or more polypeptides selected from Table 3. For example, the polypeptides corresponding to SEQ ID NOs:1-10 can be used in combination with SEQ ID NOs:84-90. In some cases, SEQ ID NOs:1, 5, and 10 can be used in combination with SEQ ID NOs:85, 90, and 100. In some cases, one or more vaccinia virus polypeptides set forth in SEQ ID NOs: 19, 29, and 49 can be used in combination with one or more vaccinia virus polypeptides set forth in SEQ ID NOs:41 and 42.

In some cases, a composition can be designed to include one or more vaccinia virus polypeptides that have a sequence present within a vaccinia virus polypeptide that is expressed during an early phase of a poxvirus infection in combination with one or more vaccinia virus polypeptides that have a sequence present within a vaccinia virus polypeptide that is expressed during a late phase of a poxvirus infection. For example, one or more vaccinia virus polypeptides set forth in Table 2 or Table 3 for ORFs A7L, D13L, D6R, DBL, E10R, E6R, EBR, G4L, H4L, H7R, and I1L (e.g., a polypeptide involved in a late phase of infection) can be used in combination with one or more vaccinia virus polypeptides set forth in Table 2 or Table 3 for ORFs A44L, A46R, A48R, A52R, A8R, B12R, B13R, B15R, B1R, C11R, C12L, C2L, E5R, E9L, F11L, F12L, F16L, F1L, HSR, J3R, J4R, J6R, K1L, K3L, K6L, K7R and N2L (e.g., a polypeptide involved in an early phase of infection). In some cases, one or more vaccinia virus polypeptides set forth in SEQ ID NOs:19 (A44L) and 49 (E5R) can be used in combination with one or more vaccinia virus polypeptides set forth in SEQ ID NOs:29 (A7L), 41 (D13L), and 42 (D13L).

In some cases, a composition can be designed to include two or more vaccinia virus polypeptides (e.g., two, three, four, five, six, seven, eight, nine, ten, or more vaccinia virus polypeptides) that potentially have the ability to bind to class I MHC molecules with high binding affinity. For example, two or more vaccinia virus polypeptides set forth in SEQ ID NOs:1, 19, 29, 37, 41, 42, 44, 49, 64, and 68 can be used in combination to form a composition (e.g., a vaccine composition).

The polypeptides provided herein (e.g., the polypeptide presented in Tables 2 and 3) can include oxidized amino acid residues (e.g., oxidized forms of methionine) or can lack oxidized amino acid residues.

The term "isolated" refers to material which is substantially or essentially free from components which normally accompany the material as it is found in its native state. Thus, isolated polypeptides as described in this document do not contain materials normally associated with the polypeptides in their in situ environment. The term "polypeptide" generally refers to a short chain of amino acids linked by polypeptide bonds. Typically, polypeptides comprise amino acid chains of about 2-100, more typically about 4-50, and most commonly about 6-20 amino acids.

Any appropriate method can be used to obtain a vaccinia virus polypeptide provided herein. For example, polypeptides having the sequence set forth in any one of SEQ ID NOs:1-116 can be synthesized by methods known to one skilled in the art of making polypeptides. Of course, other methods in the art would be appropriate. In some cases, simple chemical polypeptide synthesis techniques can be used to obtain a vaccinia virus polypeptide provided herein. In some cases, a polynucleotide sequence encoding for a vaccinia virus polypeptide of interest can be inserted into a plasmid or other vector that can then be delivered to hosts that can be induced to transcribe the polynucleotide into the polypeptide of interest. In some cases, a polynucleotide sequence for a larger polypeptide can be inserted into host cells that can produce the larger polypeptide and then process that polypeptide into a smaller polypeptide or a functionally equivalent variant of interest.

A composition provided herein containing one or more polypeptides set forth in SEQ ID NOs:1-83 of Table 2 or any appropriate combination of polypeptides as described herein can be formulated to provide a polypeptide-based vaccine. In some cases, such a vaccine can be designed to be based on a combination of naturally processed and presented vaccinia virus polypeptides. For example, a polypeptide-based vaccine can be designed to include at least one polypeptide selected from SEQ ID NOs:1-83 and at least one polypeptide selected from SEQ ID NOs:84-116. Any appropriate method can be used to formulate a polypeptide-based vaccine including, for example, those methods used to formulate polypeptide-based vaccines directed against other viral targets. Examples of polypeptide-based vaccines directed to other viral targets are described elsewhere (see, e.g., Belyakov et al., *Proc. Natl. Acad. Sci. U.S.A.*, 95(4):1709-1714 (1998) and Jackson et al., *Proc. Natl. Acad. Sci. U.S.A.*, 101(43):15440-15445 (2004)). In some cases, a vaccine composition provided herein can include one or more polypeptides set forth in SEQ ID NOs:1-83 (or any appropriate combination of polypeptides as described herein) in combination with the active ingredients or polypeptides of a vaccine composition described elsewhere (see, e.g., Belyakov et al., *Proc. Natl. Acad. Sci. U.S.A.*, 95(4):1709-1714 (1998) and Jackson et al., *Proc. Natl. Acad. Sci. U.S.A.*, 101(43):15440-15445 (2004)). Such vaccine composition can provide a level of protection against Orthopoxvirus infections as well as infections by the other viral targets.

In some cases, a vaccine composition provided herein can be designed to prevent or treat an Orthopoxvirus infection. For example, a vaccine composition provided herein can have the ability to induce a protective or therapeutic immune response within a mammal (e.g., a human). In some cases, a vaccinia virus polypeptide provided herein can be a highly conserved polypeptide across the family of Orthopoxvirus members. In such cases, a vaccine composition containing such a highly conserved polypeptide can be used to provide protection against multiple members of the Orthopoxvirus family. In some cases, a vaccine composition provided herein can be directed against any Orthopoxvirus. For example, a vaccine composition provided herein can be directed against monkeypox, cowpox, and camelpox. In some cases, a vaccine composition provided herein can be directed against vaccinia or variola major or minor. The term "vaccine" as used herein refers to immunogenic compositions that are administered to a subject for the prevention, amelioration, or treatment diseases, typically infectious diseases. In some cases, one or more features of other vaccine preparations can be incorporated into a vaccine composition provided herein. For example, a polypeptide used to create a vaccinia vaccine can be included within a vaccine composition provided herein. Examples of vaccinia-specific single polypeptide vaccines that have one or more features that can be included in the methods and materials (e.g., a vaccine composition) provided herein are described elsewhere (see, e.g., Snyder et al., *J. Virol.*, 78(13):7052-60 (2004) and Drexler et al., *Proc. Natl. Acad. Sci. U.S.A.*, 100(1):217-22 (2003)).

A polypeptide provided herein (e.g., a polypeptide set forth in Table 2 or Table 3) can be formulated into a vaccine composition using any appropriate method.

In some cases, a polypeptide provided herein can be combined with a pharmaceutically acceptable carrier or pharmaceutical excipient. The term "pharmaceutically acceptable" refers to a generally non-toxic, inert, and/or physiologically compatible composition. A term "pharmaceutical excipient" includes materials such as adjuvants, carriers, pH-adjusting and buffering agents, tonicity adjusting agents, wetting agents, preservatives, and the like. Examples of adjuvants include, without limitation, CpG, aluminum sulfate, aluminumphosphylate, and MF59. In some cases, vaccines or components of a vaccine can be conjugated to, for example, a polysaccharide or other molecule, to improve stability or immunogenicity of one or more vaccine components. In some cases, a polypeptide provided herein (e.g., a polypeptide set forth in Table 2 or Table 3) can be formulated into a vaccine composition containing cells. For example, one or more polypeptides provided herein can be included within a cellular vaccine. Any appropriate method can be used to prepare a cellular vaccine or the components of a cellular vaccine.

The methods and materials provided herein can be used in combination with other techniques having the ability to enhance the immune response of a vaccine. For example, a vaccine composition provided herein can be designed to include or to be used in combination with an effective amount of an agent that can augment the level of a TAP molecule and/or a tapasin molecule within a cell. Increasing the level of TAP and/or tapasin molecules within a cell can increase the immunogenicity of a vaccine composition containing a polypeptide provided herein. In some cases, the techniques described elsewhere (Vitalis et al., *PLoS Pathog.*, 1(4):e36 (2005)) can be used in combination with the methods and materials provided herein. Examples of TAP molecules include, without limitation, TAP-1 molecules and TAP-2 molecules. In some cases, an effective amount of an agent that can augment the level of a TAP1 molecule alone, a TAP2 molecule alone, both TAP-1 and TAP-2 molecules, a tapasin molecule alone, or the combination of TAP-1, TAP-2, and tapasin molecules can be used in combination with the methods and materials provided herein.

The levels of a TAP molecule can be augmented using agents that can increase TAP expression including, without limitation, interferon-γ and p53. In some cases, the levels of a TAP molecule or a tapasin molecule can be augmented by administering a nucleic acid molecule encoding a TAP molecule or a tapasin molecule. The target cell can be any appropriate cell to which one wishes to generate an immune response. For example, in a prophylactic therapy or a vaccine, the target cell can be an essentially normal cell (e.g., a cell expressing normal TAP levels) that may not have been otherwise exposed to an antigen. In such a case, the agent that augments TAP can be co-administered with the antigen (e.g., a polypeptide provided herein) to which one wishes to generate an immune response. For example, when used as a therapeutic, the target cell can be previously infected with a pathogen (such as a virus or bacteria).

This document also provides methods and materials for treating mammals (e.g., humans) having an Orthopoxvirus infection. For example, a composition provided herein can be administered to a mammal having an Orthopoxvirus infection under condition effective to reduce the severity of one or more symptoms of the Orthopoxvirus infection. Treatment of individuals having an Orthopoxvirus infection (e.g., a vaccinia virus infection) can include the administration of a therapeutically effective amount of one or more polypeptides set forth in SEQ ID NOs:1-83. In some cases, treatment can include the use of one or more polypeptides set forth in SEQ ID NOs:1-83 individually or as a mixture. In some cases, one or more polypeptides set forth in SEQ ID NOs:1-83 can be used in combination with at least one of the polypeptides set forth in SEQ ID NOs:84-116. The polypeptides can be used or administered as a mixture, for example, in equal amounts, or individually, provided in sequence, or administered all at once. The term "therapeutically effective amount" refers to that amount of the agent sufficient to result in amelioration of symptoms, e.g., treatment, healing, prevention or amelioration of such conditions. In providing a subject with a polypeptide provided herein (e.g., a vaccinia-derived polypeptide), combinations or fragments thereof, capable of inducing a therapeutic effect, the amount of administered agent will vary depending upon such factors as the subject's age, weight, height, sex, general medical condition, previous medical history, etc. In some cases, the amount of administered agent can vary depending upon the subject's HLA allele type. The subject can be, for example, a mammal. The mammal can be any type of mammal including, without limitation, a mouse, rat, dog, cat, horse, sheep, goat, cow, pig, monkey, or human.

This document also provides kits that can be used for a variety of applications including, without limitation, combining reagents necessary for producing vaccine compositions. Such vaccine compositions can include one or more polypeptides provided herein (e.g., one or more vaccinia-derived polypeptide described herein) as well as adjuvants, diluents, and pharmaceutically acceptable carriers. In some cases, a kit provided herein can include a combination of vaccinia virus polypeptides (e.g., vaccinia-derived polypeptides) as described herein. In some cases, a kit provided herein can include at least 2, 3, 5, 10, 15, 20, 25, 30, 35, 40, 45, 50, or more polypeptides described herein. Any appropriate combination of the polypeptides can be used. In some cases, a kit provided herein can include one or more adjuvants and can include instructions for preparing and administering a vaccine composition.

In some cases, a kit provided herein can be designed as a diagnostic kit. For example, a kit provided herein can be designed to include reagents that can be used to detect cellular immune responses. In some cases, a kit provided herein can be designed to include polypeptides that can be used to detect antigen specific T cells. Such polypeptides (e.g., a polypeptide listed in Table 2 or 3) can be used to detect antigen specific T cells in samples from Orthopoxvirus (e.g., vaccinia virus) infected or exposed subjects. In some cases, such polypeptides (e.g., a polypeptide listed in Table 2 or 3) can be used to detect antigen specific T cells post-vaccination of a subject to determine the efficacy of immunization.

Any appropriate method can be used to detect antigen specific T cells using a polypeptide provided herein. For example, flow cytometry, enzyme-linked immunospot (ELISPOT), cytokine secretion, direct cytotoxicity assays, and lymphoproliferation assays can be used to detect antigen specific T cells using a polypeptide provided herein. In some cases, flow cytometry using MHC class I tetramers can be used, particularly for vaccinia epitope specific quantitation of $CD8^+$ T cells. Such kits can include at least one polypeptide provided herein. In some cases, such a kit can include at least 2, 3, 5, 10, 15, 20, 25, 30, 35, 40, 45, 50, or more polypeptides provided herein for the detection of antigen specific T cells.

The invention will be further described in the following examples, which do not limit the scope of the invention described in the claims.

EXAMPLES

Example 1

Discovery of Naturally Processed and HLA-Presented Class I Polypeptides from Vaccinia Virus Infection using Mass Spectrometry for Vaccine Development Materials and Methods
Cell Culturing and Vaccinia Virus Infection Epstein-Barr virus (EBV)-transformed B-cells (European Collection of Cell Cultures—ECACC, number 86052111, Salisbury, Wiltshire, UK), homozygous for the HLA-A*0201, B*1501, and C*03 were of human origin and used as antigen presenting cells (APCs). The New York City Board of Health (NYCBOH, Dryvax®) vaccine-strain of Vaccinia virus was cultured in HeLa cells in Dulbecco's modified Eagle's medium, supplemented with 5% fetal calf serum (FCS; Life Technologies, Gaithersburg, Md.). B-cells were infected with live Vaccinia virus at a multiplicity of infection (moi) of 0.1 PFU/cell for 2 hours and further maintained for 24-30 hours in RPMI-1640 supplemented with 8% FCS. These uninfected and Vaccinia-infected cells (approximately $1 \times 10^9$ cells each) were used for obtaining cell lysates for the class I HLA molecules purification.

Isolation of HLA-Associated Polypeptides from Uninfected and Vaccinia-Infected Cells Class I HLA molecules were purified from human homozygous B-cells using an immunoaffinity approach, and their associated polypeptides were extracted as previously described (Slingluff et al., *J. Immunol.*, 150:2955-2963 (1993) and Johnson et al., *J. Am. Soc. Mass Spectrom.*, 16(11):1812-1817 (2005)). In brief, cells were lysed with a buffer containing 20 mM Tris, pH 8.0, 150 mM NaCl, 1% CHAPS and protease inhibitors (1 mM Pefabloc SC, Roche Applied Science, Indianapolis, Ind.). The clarified supernatants were passed over a protein A-sepharose 4B (Sigma) column containing the monoclonal antibody (mAb) W6/32 specific for HLA-A, B and C (Parham et al., *J. Immunol.*, 123(1):342-349 (1979) and Hogan et al., *Cancer Immunol. Immunother.*, 54(4):359-371 (2005)). The HLA molecules (1.2 mg/mL) were dissociated from their bound class I polypeptides using 0.2N acetic acid, pH 2.7, and polypeptides were separated from the HLA by filtration through a 10-kDa molecular mass cutoff filter (Millipore, Bedford, Mass.).

Strong Cation Exchange Fractionation

Strong cation exchange (SCX) fractionation of the sample was performed after desalting the polypeptide pool with a reversed phase 1 mm by 8 mm polypeptide trap (Michrom BioResources, Auburn, Calif.). SCX chromatography used a gradient of 5 mM $KH_2PO_4$, pH 3.0 to 0.4 M KCl of 5 mM $KH_2PO_4$, pH 3.0. Acetonitrile was added to each mobile phase to 20% by volume. Desalted polypeptides were loaded onto a polysulfoethyl aspartamide column (Michrom BioResources) at 0.5% mobile phase A, and a gradient was developed to 20% B over 20 minutes at a flow rate of 200 µL/min, then from 20% B to 80% B over the next 10 minutes. Two-minute fractions were collected; each fraction was vacuum centrifuged to dryness before analyzing the fractions by nLC-MS/MS.

LTQ-Orbitrap nLC-MS/MS Analyses

Automated nLC-MS/MS analyses were performed on a commercial linear ion trap-Fourier transform hybrid mass spectrometer (LTQ-Orbitrap, Thermo Fisher Scientific, Waltham, Mass.), interfaced to a nano-scale liquid chromatograph and autosampler (Eksigent NanoLC 1D, Dublin, Calif.), using a 15 cm by 75 µm i.d. column packed with Magic $C_{18AQ}$ (5 µm particles, 200 Å pore size, Michrom BioResources). The autosampler loaded 5-20 µL onto a 0.25 µL pre-column (Optimize Technologies, Oregon City, Oreg.), custom-packed with Magic $C_8$, 5 µm, 200 Å (Michrom BioResources). Mobile phase A consisted of water/acetonitrile/formic acid (98/2/0.2 by volume) and mobile phase B was acetonitrile/water/formic acid (90/10/0.2 by volume). A 90 minute LC method employed a gradient from 2% to 40% B over 60 minutes, followed by a second segment to 90% B at 85 minutes, with a column flow of 0.4 µL/minute. A third pump was used to load polypeptides from the autosampler to the pre-column, with 0.05% TFA and 0.15% formic acid in water at 15 µL/minute.

SCX fractions were analyzed multiple times by nLC-MS/MS using data-dependent acquisition of tandem mass spectra. The first experiment targeted singly charged precursors between 750 and 1500 on the m/z (molecular mass m divided by charge z) scale. A second experiment targeted doubly and triply charged precursors between m/z 375 and 750, consistent with MHC class I polypeptides which are predominantly 9-11 amino acids long.

The LTQ-Orbitrap was operated in a data-dependent mode, first acquiring an Orbitrap survey scan with 60,000 resolving power (FWHM at m/z 400), a target cell population of $1 \times 10^6$ ions, and a maximum ion fill time of 300 ms. The preview Fourier transform was used to select the five most abundant ions for MS/MS experiments in the LTQ. LTQ MS/MS spectra were acquired with a 2.5 mass unit isolation width, target ion population of $1 \times 10^4$ ions, one microscan, maximum ionization fill time of 100 ms, normalized collision energy of 35%, activation Q of 0.25, and activation time of 30 ms. Once ions were selected for MS/MS, they were subsequently excluded for 45 seconds. The exclusion window was 1 m/z below, and 1.6 m/z above the exclusion mass.

Polypeptide Identification from MS/MS Data

Database searching was performed using the SWIFT workflow tool developed in-house. SWIFT coordinates the generation of database search files (using extract_msn software from ThermoFisher Scientific), initiates database searches using MASCOT, Sequest, and X!Tandem search engines, and integrates these search results using Scaffold (Ver. 1_07_00, Proteome Software, Portland, Oreg.). Database searches were done against a subset of the SwissProt database (January 2007) obtained using the Bioworks 3.2 (Thermo Fisher) database utility to select human, bovine, and vaccinia proteins. Bovine proteins were included in the database since cell cultures were supplemented with fetal calf serum. Database searches were performed with a precursor mass tolerance of 7 parts-per-million (ppm), fragment ion mass tolerance of 0.6 mass units, and without any protease specificity. Single oxidation on methionine residues was considered as a variable modification. The database was appended with decoy protein entries consisting of randomized protein sequences (MASCOT utility) for estimating the false-positive rate resulting in a database of 43,400 entries (including the randomized decoy entries). Results from all analyses of all SCX fractions were combined by Scaffold and exported to an Excel spreadsheet.

The Scaffold program (Proteome Software) was used to combine search results from all of the LC-MS/MS analyses and to calculate polypeptide identification probabilities using Scaffold's implementation of PolypeptideProphet (Keller et al., *Anal. Chem.*, 74(20):5383-5392 (2002) and Nesvizhskii et al., *Anal. Chem.*, 75(17): 4646-4658 (2003)). An export function within Scaffold (Spectrum Report) was used to create a text file of all search results passing a lenient filter threshold of 80% protein probability, with at least 1 polypeptide identified above an 80% polypeptide probability threshold; 23,800 search results met those criteria, 1521 of these were from decoy polypeptides. Additional filtering was then applied to this dataset while estimating the false-positive rate (FPR) of identifications from the incidence of identifications from the decoy database using the formula: 2×# matches to decoy polypeptides/(number of true positives+number of false positives) as described elsewhere (Elias et al., *Nat. Methods*, 4(3):207-214 (2007)). The FPR was calculated as a function of thresholds for the following scoring parameters: Sequest cross-correlation score (XCorr), the difference between the top two normalized cross-correlation scores ($\Delta C_n$), Mascot Ion Score, and mass error of the precursor mass.

Results

HLA Class I Polypeptide Identification by Tandem Mass Spectrometry

FIG. 1 provides an overview of the protocol used to sequence HLA class I polypeptides isolated from B-cells after infection with vaccinia. Sixteen strong cation exchange fractions were analyzed by nano-scale liquid chromatography coupled with tandem mass spectrometry (nLC-MS/MS) on the LTQ-Orbitrap. Two data sets were acquired, each using multiple injections as described above. The initial data set was acquired with external mass calibration, followed by a second data set collected with internal mass calibration using lock masses at m/z 391.2843 and m/z 445.1200 as described elsewhere (Olsen et al., *Mol. Cell Proteomics*, 4(12):2010-2021 (2005)). These analyses generated 214,800 MS/MS spectra that were searched against the human, bovine, and Vaccinia subset of proteins in the SwissProt database (January 2007 version).

Polypeptide sequencing by mass spectrometry involves matching MS/MS fragmentation spectra against theoretical fragmentation spectra calculated for any polypeptide sequence in the database within a tolerance window of the molecular weight of the polypeptide as measured by the mass spectrometer. As a result, every database search will return a result, and each of these matches to a sequence must be evaluated for their validity. A variety of scoring metrics exist from which a threshold is established for accepting or rejecting the search result from any MS/MS spectrum. The goal of that threshold is to minimize the number of incorrect or random matches that are accepted (false positives) while also trying to minimize the rejection of correct sequence matches (false negatives). Most of these scoring criteria have been developed within the context of identifying polypeptides generated from cleavage of proteins with trypsin. Trypsin cleaves on the C-terminal side of arginine and lysine and this cleavage specificity greatly reduces the list of candidate polypeptide sequences that are matched against the experimental spectra. The basic C-terminus of tryptic polypeptides provided by the Arg and Lys side chains, favorably directs fragmentation during MS/MS, influencing the scores from the database search results.

HLA class I polypeptides are not constrained to a basic C-terminal amino acid. For most common alleles, hydrophobic amino acids predominate in the C-terminal position, though basic residues such as Lys, Arg, Pro, or His, are often found somewhere in the C-terminal half of the polypeptide. Also not requiring Lys or Arg as the C-terminal amino acid from the database, greatly increases the number of candidate sequences whose theoretical fragmentation spectrum must be matched against the experimental fragmentation spectrum. Because of these differences we implemented the use of decoy database entries during the search as described elsewhere (Elias et al., *Nat. Methods*, 4(3):207-214 (2007)). For each protein in the database an additional entry is created with its amino acid sequence randomized, and labeled as such, in its accession identifier. During the database search these decoy proteins compete against authentic proteins for the best match to experimental spectra. Search results that identify polypeptides from a decoy protein are known to be incorrect. The rate of matches to polypeptides from the decoy proteins is used to estimate the false-positive rate as described above (*Polypeptide identification from MS/MS data*).

Search results are summarized in Table 1 at the estimated 1% and 5% FPR. 5915 MS/MS spectra were identified at the 1% FPR (30 matches against decoy polypeptides), representing 2731 unique sequences. 65 of these polypeptides were unique to vaccinia virus, originating from 44 vaccinia virus proteins. At the 5% FPR, the number of matched spectra increased from 5915 to 12,819 (313 matches against decoy polypeptides), 5601 of which were unique sequences. Of these 5601 unique sequences, 116 polypeptides originated from 61 vaccinia proteins.

TABLE 1

Summary of polypeptides identified by two-dimensional liquid chromatography and tandem mass spectrometry.

|  | 1% FPR[a] | 5% FPR[a] |
|---|---|---|
| # MS/MS spectra identified[b] | 5915 | 12819 |
| # Unique sequences[c] | 2731 | 5601 |
| # Unique vaccinia sequences[d] | 65 | 116 |
| # Vaccinia proteins represented[e] | 44 | 61 |

[a]Database search results summarized at the 1% false positive rate (FPR) and the 5% FPR.
[b]Number of tandem mass spectrometry (MS/MS) search results surpassing scoring thresholds that characterize the 1% and 5% FPR. Includes results for polypeptides identified in multiple strong cation exchange fractions, multiple MS/MS spectra from the same precursor m/z, at multiple charge states, and from multiple database entries containing the identified sequence.
[c]Number of unique polypeptide sequences identified, from all species represented in the database (human, bovine, vaccinia proteins).
[d]Number of polypeptide sequences identified that are unique to vaccinia proteins.
[e]Number of vaccinia proteins represented by the identified vaccinia polypeptides.

The naturally processed and presented vaccinia polypeptides identified were listed in Table 2 and Table 3. The polypeptides were sorted by the open reading frame (ORF) they originated from and were marked whether they were identified within database search scoring criteria that characterized the 5% FPR (italicized) or the 1% FPR (non-italicized). Vaccinia polypeptide sequences identified at the 5% or better FPR were selected for additional studies to characterize their immunogenic properties.

TABLE 2

Class I polypeptides from Vaccinia virus identified by two-dimensional liquid chromatography and tandem mass spectrometry after Vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 1 | ILIRGIINV | A ORF T | C, V | None | A*0201 | | | |
| 2 | AQITTDDLVKSY | A10L | C, V | Vr, Cm, Cw, Mn, Ra | B*1501 | | | |
| 3 | *VQAVTNAGKIVY* | A12L | A, C, V | Vr, Cm, Cw, Mn, Ra | B*1501 | | | |
| 4 | *S<sup>ox</sup>MADVSIKTNSV* | A1L | A, C, V | Cm, Cw | A*0201 | | | |
| 5 | LLFEDIIQNEY | A23R | A, C, T, V | Vr, Cm, Cw, Mn | B*1501 | | 114 | |
| 6 | FTVNIFKEV | A24R | A, C, T, V | Vr, Cm, Cw, Mn, Ra | A*0201 | 8.4 | 195 | 16 |

TABLE 2-continued

Class I polypeptides from Vaccinia virus identified by two-dimensional
liquid chromatography and tandem mass spectrometry
after Vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 7 | *GDKFTTRTSQKGTVAY* | A24R | A, C, T, V | Vr, Cm, Cw, Mn, Ra | B*1501 | | | |
| 8 | ILYDPETDKPY | A24R | A, C, T, V | Vr, Cm, Cw, Fw, Mn, Ra | B*1501 | | 81 | |
| 9 | *TTRTSQKGTVAY* | A24R | A, C, T, V | Vr, Cm, Cw, Mn, Ra | B*1501 | | | |
| 10 | VIINSTSIF | A24R | A, C, T, V | Vr, Cm, Cw, Mn, Ra | B*1501 | 10.0 | 223 | 13 |
| 11 | LTREMGFLVY | A29L | A, C, T, V | Vr, Cm, Cw, Mn, Ra | B*1501 | 17.4 | 132 | 15 |
| 12 | TVINEDIVSKLTF | A29L | A, C, T, V | Vr, Cm, Cw, Mn, Ra | B*1501 | | | |
| 13 | TLRFLEKTSF | A31R | C, V | Vr, Cm, Cw, Mn | B*1501 | 72.0 | 507 | 11 |
| 14 | VQIDVRDIKY | A35R | C, V | Cm, Cw | B*1501 | 52.8 | 131 | 23 |
| 15 | YIIGNIKTV | A35R | C, V | Cm, CwRa | A*0201 | 101.2 | 143 | 29 |
| 16 | IQYPGSEIKGNAY | A44L | A, V | Cm, Cw | B*1501 | | | |
| 17 | IQYPGSKIKGNAY | A44L | C | Ra | B*1501 | | | |
| 18 | *IQYPGSKIKGNAYF* | A44L | C | Ra | B*1501 | | | |
| 19 | KISNTTFEV | A44L | A, C, V | Cm, Cw, Mn, Ra | A*0201 | 194.1 | 10 | 23 |
| 20 | LLISADDVQEIRV | A44L | A, C, V | Vr, Cm, Cw, Mn, Ra | A*0201 | | | |
| 21 | *TLYDISPGHVYA* | A44L | A, C, V | Cm, Cw, Mn, Ra | NA | | | |
| 22 | *YPGSKIKGNAY* | A44L | C | Ra | B*1501 | | 8.183 | |
| 23 | FQQKVLQEY | A46R | C, V | Vr, Cm, Cw, Ra | B*1501 | | 476 | |
| 24 | FQQKVLQEY | A48R | A, C, T, V | Vr, Cm, Cw, Mn, Ra | B*1501 | 160.0 | 112 | 21 |
| 25 | VAYAAAKGASM | A48R | A, C, T, V | Cm, Cw, Ra | NA | | 14.028 | |
| 26 | I$^{ox}$MNNPDFKTTY[h] | A49R | C, V | Vr, Cw | B*1501 | | 97 | |
| 27 | VQKQDIVKLTVY | A52R | C, V | Cw | B*1501 | | | |
| 28 | *KLFNEDLSSKY* | A7L | A, C, T, V | Vr, Cw, Mn | B*1501 | | 183 | |
| 29 | LIQEIVHEV | A7L | A, C, T, V | Vr, Cm, Cw, Mn | A*0201 | 153.3 | 18 | 29 |
| 30 | LVIENDSQF | A8R | A, C, V | Vr, Cm, Cw | B*1501 | 1.1 | 215 | 19 |
| 31 | *KLYKSGNSHIDY* | B12R | A, C, V | Cw, Ra | B*1501 | | | |
| 32 | RVFAPKDTWSVF | B12R | A, C, V | Cw, Ra | B*1501 | | | |
| 33 | KVSAQNISF | B13R | C, V | Vr, Cm, Cw, Mn, Ra | B*1501 | 2.4 | 117 | 7 |
| 34 | GQLYSTLLSF | B15R | C, V | Vr, Cm, Ra | B*1501 | 96.0 | 106 | 21 |
| 35 | LQYAPRELLQY | B1R | A, C, V | Vr, Cm, Cw, Mn | B*1501 | | 78 | |
| 36 | *HCYL$^{ox}$MNEGFES* | B21R, C15L | C | Cw | NA | | 39.041 | |
| 37 | $^{ox}$MLINYL$^{ox}$MLL | C11R | A, T | None | A*0201 | 83.5 | 4 | 27 |
| 38 | *KIKDDFQTVNF* | C12L | C, V | Vr, Cm, Cw, Mn | B*1501 | 731 | | |
| 39 | *KIYGSDSIEF* | C12L | C, V | Vr, CwMn | B*1501 | 14.4 | 229 | 12 |
| 40 | *YV$^{ox}$MGGVYTTY* | C2L | C, T, V | Cm, Cw, Ra | B*1501 | 6.3 | 68 | 23 |
| 41 | KLSDSKITV | D13L | A, C, T, V | Vr, Cm, Cw, Mn | A*0201 | 998.1 | 21 | 24 |

TABLE 2-continued

Class I polypeptides from Vaccinia virus identified by two-dimensional
liquid chromatography and tandem mass spectrometry
after Vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 42 | VLSLELPEV | D13L | A, C, T, V | Vr, Cm, Cw, Mn | A*0201 | 271.9 | 14 | 28 |
| 43 | *ILVPNINILKI* | D6R | A, C, T, V | Vr, Cm, Cw, Mn | NA | | 78 | |
| 44 | *I^ox MSESYTLKEV* | D6R | A, C, T, V | Vr, Cm, Cw, Fw, Mn, Ra | A*0201 | | 46 | |
| 45 | *RLKPLDIHY* | D8L | A, C, T, V | Cm, Cw, Ra | B*1501 | 172.8 | 135 | 23 |
| 46 | *YAIDVSKVKPL* | E10R | C | Vr, Cm, Cw, Mn | A*0201 | | 1.337 | |
| 47 | *GKASQNPSK^ox MVY* | E5R | C, D | Cw, Ra | B*1501 | | | |
| 48 | *IGKASQNSPK^ox MVY* | E5R | C, D | Cw, Ra | B*1501 | | | |
| 49 | KLFSDISAI | E5R | C, D, V | Vr, Cm, Cw, Ra | NA | 310.7 | 8 | 25 |
| 50 | *SQNPSK^ox MVY* | E5R | C, D | Cw, Ra | B*1501 | 52.8 | 88 | 22 |
| 51 | *LARLGLVL* | E6R | C, V | Vr, Cm, Cw, Mn, Ra | A*0201 | | | |
| 52 | *GSFSGRYVSY* | E8R | C, V | Vr, Cm, Cw, Mn, Ra | B*1501 | 1.2 | 204 | 15 |
| 53 | KQKFPYEGGKVF | E9L | A, C, V | Vr, Cm, Cw, Ra | B*1501 | | | |
| 54 | IQHRQQLELAY | F11L | C, P | Ra | B*1501 | | 83 | |
| 55 | IQKDINITH | F11L | C, P | Vr, Cm, Cw, Ra | NA | 0.0 | 42.108 | 4 |
| 56 | *MLTEFLHYC* | F11L | C, P | Vr, Cw, Mn, Ra | NA | 1,664.5 | 105 | 17 |
| 57 | *LF^ox MDEIDHESY[h]* | F12L | C, P | Vr, Cm, Cw, Mn, Ra | B*1501 | | 566 | |
| 58 | *VQILMKTANNY* | F12L | C | Vr, Cm | B*1501 | | 106 | |
| 59 | *KQISISTGVLY* | F16L | C | Vr, Cm, Cw, Mn | B*1501 | | 85 | |
| 60 | *RVKQISISTGVLY* | F16L | C | Vr, Cm, Cw, Mn | B*1501 | | | |
| 61 | *IL^ox MDNKGLGVRL* | F1L | A, C, P, T, V | Cw | A*0201 | | | |
| 62 | RQLPTKTRSY | F1L | A, C, P, T, V | Vr, Cm, Cw, Mn, Ra | B*1501 | 96.0 | 80 | 25 |
| 63 | ILKSEIEKATY | G4L | C, V | Cw | B*1501 | | 374 | |
| 64 | ILIEIIPKI | H4L | A, C, V | Vr, Cm, Cw, Mn, Ra | NA | 167.2 | 4 | 31 |
| 65 | ITNKADTSSF | H5R | C, V | Vr | B*1501 | 2.6 | 276 | 10 |
| 66 | IIKEDISEY | H7R | A, C, T, V | Vr, Cm, Cw, Mn, Ra | B*1501 | 42.9 | 171 | 19 |
| 67 | YSKKFQESF | I1L | A, C, P, T, V | Cm, Cw, Mn | B*1501 | 6.0 | 185 | 11 |
| 68 | KLLLGELFFL | J3R | A, C, V | Vr, Cm, Cw, Mn | A*0201 | 20,297.3 | 7 | 27 |
| 69 | *KQKGHNKFPVNF* | J4R | C, V | Vr, Cm, Cw, Mn | B*1501 | | | |
| 70 | *VVIGNTLIKY* | J6R | A, C, V | Vr, Cw, Mn, Ra | B*1501 | 2.9 | 242 | 22 |
| 71 | *K^ox MIIEKHVEY* | K1L | C, V | None | B*1501 | 2.4 | 103 | 16 |
| 72 | *^ox MIIEKHVEY* | K1L | C, V | None | B*1501 | 13.2 | 154 | 18 |
| 73 | SLLFIPDIKL | K1L | C, V | Vr, Cw, Mn, Ra | A*0201 | 79.0 | 61 | 25 |
| 74 | *SQFDDKGNTALY* | K1L | C, V | Cm, CwMn, Ra | B*1501 | | | |
| 75 | *VLLDDAEIAK^ox M* | K1L | V | Cm, Cw, Mn, Ra | NA | | 55 | |

TABLE 2-continued

Class I polypeptides from Vaccinia virus identified by two-dimensional
liquid chromatography and tandem mass spectrometry
after Vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 76 | VLLDDAEIAK$^{ox}$MII[h] | K1L | V | Cm, Cw, Mn, Ra | NA | | | |
| 77 | *KLVGKTVKV* | K3L | C, V | Cm, Cw, Mn | A*0201 | 243.3 | 54 | 30 |
| 78 | *ITYPKALVF* | K6L | C, V | Cw, Mn | B*1501 | 4.1 | 168 | 11 |
| 79 | *MMIDDFGTARGNY* | K6L | C, V | None | B*1501 | | | |
| 80 | *L$^{ox}$MKFDDVAIRY* | K7R | A, C, V | Cw | B*1501 | | 147 | |
| 81 | RLYKEL$^{ox}$MKF[h] | K7R | A, C, V | Cm, Cw, Ra | B*1501 | 40.0 | 763 | 20 |
| 82 | HIIKEFMTY | N2L | C, V | Vr, Cm, Cw, Mn, Ra | B*1501 | 11.0 | 797 | 18 |
| 83 | SIIAILDRF | N2L | V | Vr, Cm, Cw, Ra | B*1501 | 20.0 | 3.775 | 16 |

[a]Non-italicized polypeptides were identified at a 1% false positive identification rate (1% FPR); italicized polypeptides were identified within scoring criteria characteristic of a 5% FPR. Polypeptide sequences in boldface are predicted to be strong binders (IC$_{50}$ < 50 nM) by the epitope prediction algorithm at: http://www.cbs.dtu.dk/services/NetMHC/ (accessed Jan. 4, 2008). $^{ox}$M denotes that the polypeptide contains an oxidized methionine (not considered incalculation of IC$_{50}$ values).
[b]Epitope is common to the following vaccinia strains: A, Ankara; C, Copenhagen; D, Dairen I; P, L-IVP; T, Tian Tan; V, Western Reserve as listed in the SwissProt database.
[c]Epitope also found in the following common poxviruses: Vr, variola; Cm, camelpox; Cw, cowpox; Fw, fowlpox; Mn, monkeypox; Ra, rabbitpox; None, not found in other poxviruses as reported in the NCBI nr database (http://www.ncbi.nlm.nih.gov/).
[d]Putative association of polypeptide with A*0201 or B*1501 alleles based upon the C-terminal amino acid: amino acids V and L classified as A2; amino acids F and Y classified as B15; NA, not assigned.
[e]Score is proportional to predicted affinity. Bioinformatics and Molecular Analysis Section, National Institute of Health, http://www-bimas.cit.nih.gov/molbio/hla bind/
[f]Center for Biological Sequence Analysis, Technical University of Denmark, http://www.cbs.dtu.dk/services/NetMHC/
[g]Score is proportional to predicted affinity. Department of Immunology, University of Tübingen, http://www.syfpeithi.de/
[h]Polypeptide was identified withoxidized and non-oxidized forms of methionine
[i]Polypeptide was identified in four oxidative forms: without methionine oxidation, oxidized at the N-terminal methionine, oxidized at the position-7 methionine, and oxidized at both methionines.

TABLE 3

Class I polypeptides from vaccinia virus identified by two-dimensional
liquid chromatography and tandem mass spectrometry
after vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 84 | GLLDRLYDL | O1L | C, V | Cm, Cw, Ra | A*0201 | 745.4 | 10 | 29 |
| 85 | IVIEAIHTV | A48R | A, C, T, V | Vr, Cm, Cw, Mn, Ra | A*0201 | 97.6 | 53 | 27 |
| 86 | ILSDENYLL | A6L | C, V | Vr, Cm, Cw, Mn, Ra | A*0201 | 148.9 | 10 | 24 |
| 87 | ILDDNLYKV | G5R | C | Vr, Cm, Cw, Mn, Ra | A*0201 | 446.0 | 4 | 30 |
| 88 | KLFTHDIML | D12L | A, C, V | Vr, Cm, Mn | A*0201 | 276.6 | 15 | 22 |
| 89 | KIDYYIPYV | E2L | C, V | Vr, Cm, Cw, Mn, Ra | A*0201 | 169.4 | 2 | 24 |
| 90 | FLTSVINRV | F12L | C | Vr, Cm, Cw, Mn, Ra | A*0201 | 735.9 | 5 | 25 |
| 91 | NLFDIPLLTV | F12L | C, P | Vr, Cm, Cw, Mn, Ra | A*0201 | 2,426.7 | 7 | 29 |
| 92 | *$^{ox}$MQKFTILEY*[h] | | A, C, V | Vr, Cm, Cw, Mn | B*1501 | 288.0 | 65 | 23 |
| 93 | SQIFNIISY | A17L | C, V | Vr, Cm, Cw, Mn | B*1501 | 96.0 | 74 | 9 |
| 94 | ALDEKLFLI | A23R | A, C, T, V | Vr, Cm, Cw, Mn | NA | 228.2 | 6 | 27 |

TABLE 3-continued

Class I polypeptides from vaccinia virus identified by two-dimensional
liquid chromatography and tandem mass spectrometry
after vaccinia infection of human B-cells.

| SEQ ID NO: | Polypeptide sequence[a] | ORF | Vaccinia strain[b] | Other pox viruses[c] | Putative allele[d] | BIMAS[e] | CBS IC50 (nM)[f] | SYFPEITHI[g] |
|---|---|---|---|---|---|---|---|---|
| 95 | HMIDKLFYV | A23R | A, C, T, V | Vr, Cm, Cw, Mn | A*0201 | 513.8 | 2 | 26 |
| 96 | *QIDVRDIKY* | A35R | C, V | Cm, Cw | B*1501 | 1.8 | 12.810 | 16 |
| 97 | SIMDFIGPYI | A35R | C, V | Cm, Cw, Mn, Ra | NA | 119.7 | 11 | 21 |
| 98 | *YAAAKGASM* | A48R | A, C, T, V | Cm, Cw, Ra | NA | 0.3 | 4.895 | 17 |
| 99 | ILQNRLVYV | A52R | C, V | Cw | A*0201 | 1,495.7 | 13 | 28 |
| 100 | *IQFMHEQGY* | B1R | A, C, V | Vr, Cm, Cw, Mn | B*1501 | 52.0 | 106 | 21 |
| 101 | *TLLDHIRTA* | B22R, C16L | C | Cw, Ra | NA | 34.7 | 84 | 23 |
| 102 | *RQFYNANVL* | C2L | C, T, V | Cm, Cw, Ra | A*0201 | | 6.960 | 11 |
| 103 | *ILKINSVKY* | D12L | A, C, V | Vr, Cm, Mn | B*1501 | 187.2 | 309 | 22 |
| 104 | LLLETKTILV | E9L | A, C, V | Vr, Cm, Cw, Mn, Ra | A*0201 | 1,793.7 | 11 | 26 |
| 105 | SLSNLDFRL | F11L | C, P | Cw, Mn, Ra | A*0201 | 123.9 | 30 | 23 |
| 106 | IL$^{ox}$MDNKGLGV | F1L | A, C, P, T, V | Cw | A*0201 | 1,793.7 | 8 | 26 |
| 107 | *QLIYQRIYY* | F2L | C, P, V | Vr, Cm, Cw, Mn, Ra | B*1501 | 26.4 | 250 | 21 |
| 108 | SLKDVLVSV | G5.5E | A, C, T, V | Vr, Mn | A*0201 | 23.0 | 18 | 30 |
| 109 | *VPLPCQL$^{ox}$MY* | G5R | C | Vr, Cm, Cw, Mn, Ra | B*1501 | 2.8 | 18.814 | 12 |
| 110 | *NTIDKSSPL* | I1L | A, C, T, V | Mn | A*0201 | 1.2 | 3.795 | 18 |
| 111 | *TQFNFNGHTY* | I1L | A, C, P, T, V | Cm, Cw, Mn | B*1501 | 88.0 | 70 | 22 |
| 112 | Y$^{ox}$MIERFISF[h] | J6R | A, C, V | Vr, Cm, Cw, Mn, Ra | B*1501 | 2.6 | 49 | 11 |
| 113 | YLFDYPHFEA | K3L | V | None | NA | 2,010.7 | 8 | 20 |
| 114 | *IINDKGKQY* | M1L | C, V | Vr, Cw, Mn, Ra | B*1501 | 14.3 | 423 | 18 |
| 115 | *QAIEPSGNNY* | M1L | C, V | Cw, Ra | B*1501 | 2.2 | 146 | 12 |
| 116 | *ILFRMIETY* | N1L | C, V | Vr, Cw | B*1501 | 57.2 | 208 | 24 |

[a]Non-italicized polypeptides were identified at a 1% false positive identification rate (1% FPR); italicized polypeptides were identified within scoring criteria characteristic of a 5% FPR. Polypeptide sequences in boldface are predicted to be strong binders (IC$_{50}$ < 50 nM) by the epitope prediction algorithm at: http://www.cbs.dtu.dk/services/NetMHC/ (accessed Jan. 4, 2008). $^{ox}$M denotes that the polypeptide contains an oxidized methionine (not considered incalculation of IC$_{50}$ values).
[b]Epitope is common to the following vaccinia strains: A, Ankara; C, Copenhagen; D, Dairen I; P, L-IVP; T, Tian Tan; V, Western Reserve as listed in the SwissProt database.
[c]Epitope also found in the following common poxviruses: Vr, variola; Cm, camelpox; Cw, cowpox; Fw, fowlpox; Mn, monkeypox; Ra, rabbitpox; None, not found in other poxviruses as reported in the NCBI nr database (http://www.ncbi.nlm.nih.gov/).
[d]Putative association of polypeptide with A*0201 or B*1501 alleles based upon the C-terminal amino acid: amino acids V and L classified as A2; amino acids F and Y classified as B15; NA, not assigned.
[e]Score is proportional to predicted affinity. Bioinformatics and Molecular Analysis Section, National Institute of Health, http://www-bimas.cit.nih.gov/molbio/hla bind/
[f]Center for Biological Sequence Analysis, Technical University ofDenmark, http://www.cbs.dtu.dk/services/NetMHC/
[g]Score is proportional to predicted affinity. Department of Immunology, University of Tübingen, http://www.syfpeithi.de/
[h]Polypeptide was identified withoxidized and non-oxidized forms of methionine
[i]Polypeptide was identified in four oxidative forms: without methionine oxidation, oxidized at the N-terminal methionine, oxidized at the position-7 methionine, and oxidized at both methionines.

Figure 2B:
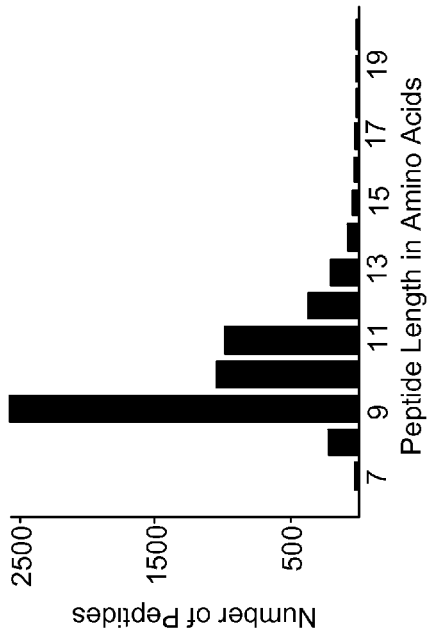
FIG. 2 contains graphs plotting the distribution of HLA polypeptide amino acid length for (A) vaccinia virus polypeptides and (B) all identified polypeptides, and the putative sorting of polypeptides by binding allele for (C) vaccinia virus polypeptides and (D) all identified polypeptides. Polypeptides were classified by allele using their C-terminal amino acid: L or V assigned to A*0201, F or Y assigned to B*1501, and all other polypeptides marked as NA (not assigned).
Figure 2D:
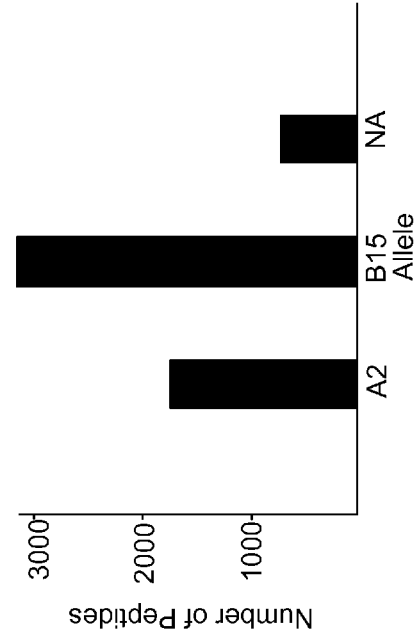
Figure 2A:
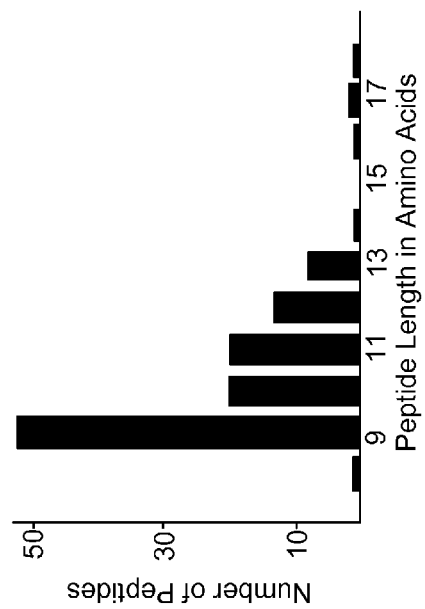
Figure 2C:
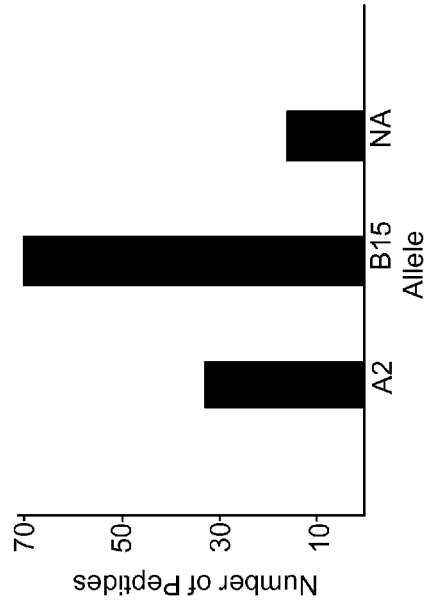

FIG. 2 shows the distribution of polypeptide lengths and putative allele from the Vaccinia subset (FIG. 2A) as well as all class I polypeptides identified at the 5% FPR rate (FIG. 2B). The majority of the polypeptides were 9-mers in both the full set of polypeptides as well as the Vaccinia subset. However, there were a significant number of polypeptides longer than 11 amino acids in the full set of identified polypeptides as well as in the Vaccinia subset. Since the W6/32 antibody used to isolate the HLA-polypeptide complexes had affinity for each of the major HLA class I alleles, the list of identified polypeptides reflected the allotypes of the host cell line; in this case HLA-A*0201, B*1501, and C*03. As a first approximation, identified polypeptides were associated with an allele by comparing the C-terminal amino acid to the reported binding motifs at the P9 position (Rammensee et al., Immunogenetics, 41:178-228 (1995)). Polypeptides terminating in L or V were assigned to A*0201, and polypeptides terminating in F or Y were assigned to B*1501, while the remaining polypeptides were designated as "not assigned." FIGS. 2C and 2D shows an estimate of the distribution of polypeptides among the A and B alleles, and while the method of associating a polypeptide with its putative allele was rudimentary, it clearly showed a significant subset of the polypeptides being presented by the B allele. There was also an unknown contribution of polypeptides from the HLA-C allele, although the density of HLA-C molecules on the surface of cells has been reported as being 6-fold less than that of the A and B alleles (Snary et al., Eur. J. Immunol., 7(8):580-585 (1977) and Neisig et al., J. Immunol., 160(1):171-179 (1998)).

Figure 3A:
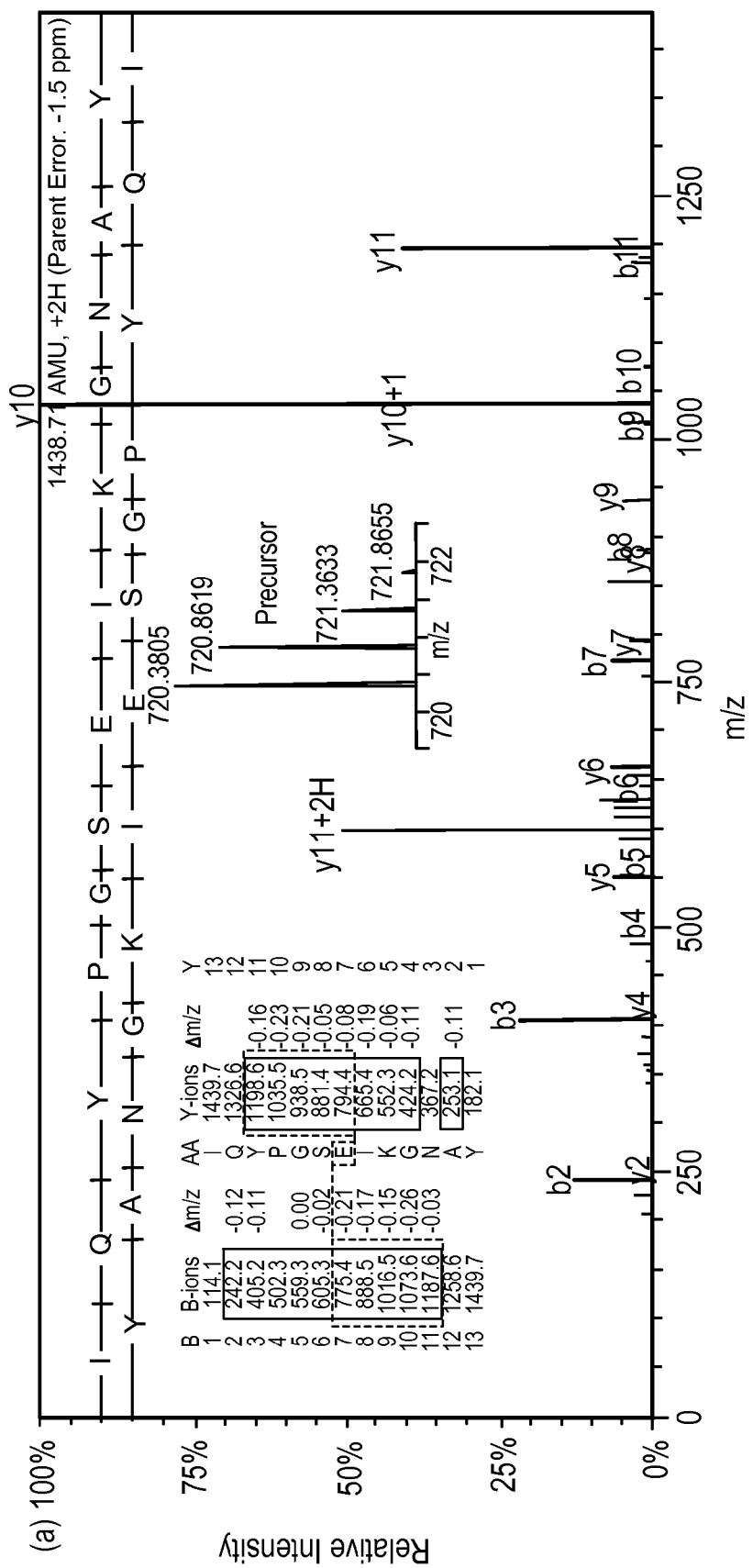
FIG. 3A is a graph of the MS/MS spectrum of the vaccinia virus polypeptide IQYPGSEIKGNAY (SEQ ID NO:16) found in SCX fractions 4 and 5, as annotated by Scaffold, including mass accuracy of the precursor mass in parts-per-million (ppm). A table of the fragment ions matched and the experimental error of the fragment ions is included. The Orbitrap survey spectrum of the precursor ion is shown.
Figure 3B:
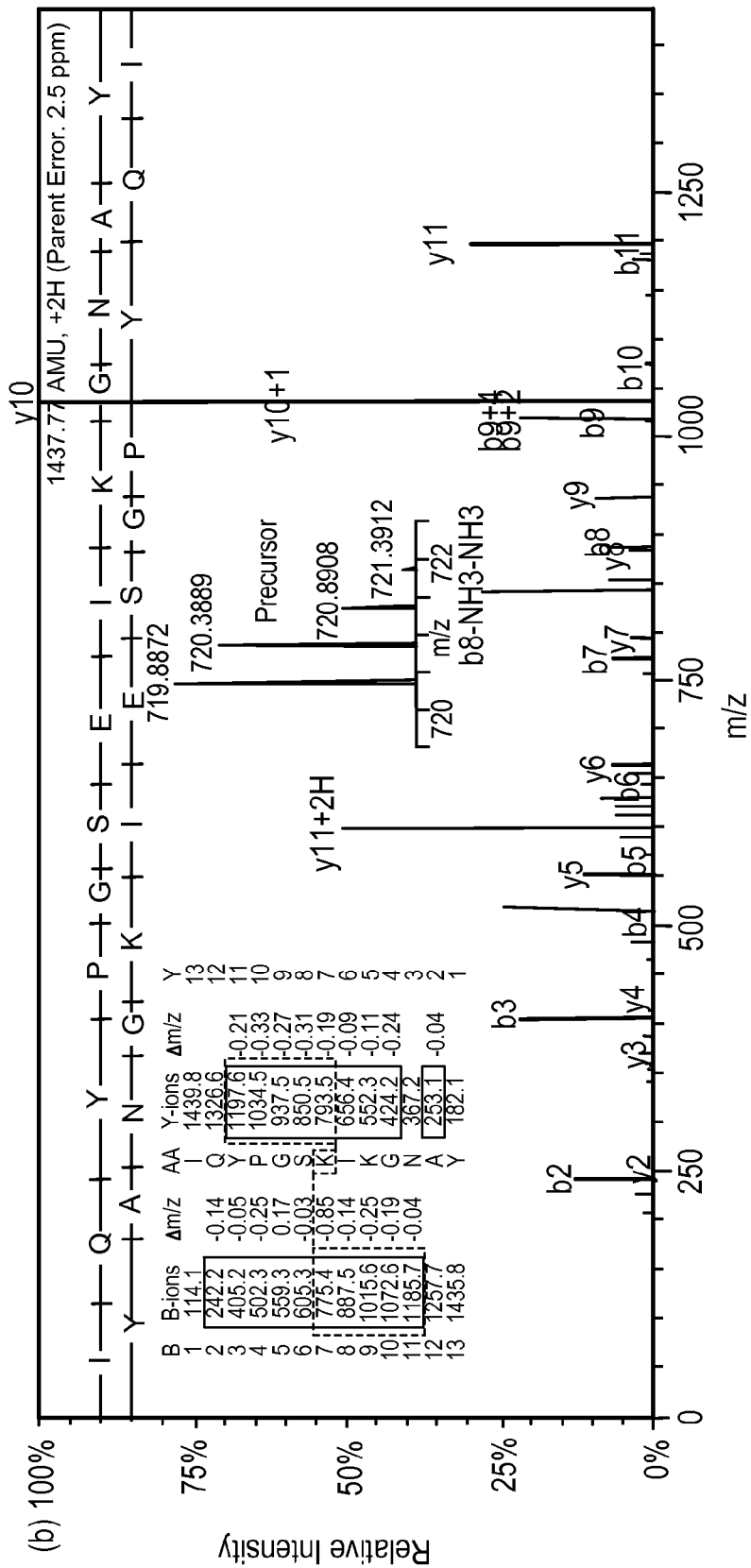
FIG. 3B is a graph containing the same information for the vaccinia virus polypeptide IQYPGSKIKGNAY (SEQ ID NO:17) as identified from SCX fractions 14-16. Note the different precursor mass, as well as concomitant changes to fragment ion masses consistent with the change in amino acid E (Glu) to K (Lys).

The vaccinia polypeptides identified also beared evidence of the genetic heterogeneity of the Dryvax strain (Osborne et al., Vaccine, 25(52):8807-8832 (2007)). For example, two forms of the same polypeptide from ORF A44L were identified: IQYPGSKIKGNAY (SEQ ID NO:17) from the Copenhagen strain, and IQYPGSEIKGNAY (SEQ ID NO:16) from the Western Reserve and Ankara strains of vaccinia. At first glance, these two sequences were flagged as redundant identities of the same polypeptide, since they varied only in one amino acid residue resulting in a mass difference of one Dalton. However, these sequences were assigned from two distinctly different polypeptides with IQYPGSEIKGNAY (SEQ ID NO:16) identified from SCX fractions 4 and 5, and IQYPGSKIKGNAY (SEQ ID NO:17) identified from SCX fractions 14-16. FIGS. 3A and 3B shows the annotated MS/MS spectra for the two polypeptides. Orbitrap spectra for each precursor mass (inset) illustrated the difference in mass for the two polypeptides (0.5 on the m/z axis, where z=2 as shown by the isotope spacing). Fragment ions were observed from the N-terminal end of the polypeptide (b-ions, highlighted in dark gray) and from the C-terminal end of the polypeptide (y-ions, highlighted in light gray), while the y- and b-ions highlighted within the dashed box delineated the sequence difference between the two polypeptides. Table 2 and Table 3 contains other instances where polypeptides were identified that were unique to specific Vaccinia strains.

Figure 4:
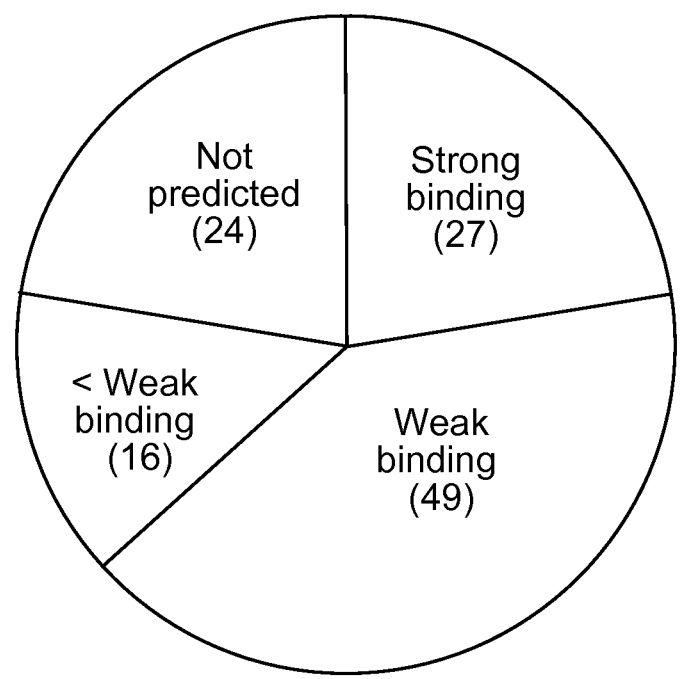
FIG. 4 is a pie graph of vaccinia epitopes directly identified by MS/MS that are classified by predicted HLA-binding strength as determined by the netMHC algorithm at the Center for Biological Sequence Analysis, Technical University of Denmark, ("http" colon, slash, slash "www" dot "cbs.dtu.dk" slash "services" slash "NetMHC" slash). Polypeptide sequences with calculated $IC_{50}$ values<50 nM were classified as strong binding, $IC_{50}$ values between 50 nM and 500 nM were classified as weak binding, and $IC_{50}$>500 nM were classified as non-binding polypeptides.

Comparison of Directly Identified Vaccinia Class I Polypeptides to Predictive Algorithms The Vaccinia protein sequences represented by this set of polypeptides were submitted to three algorithms for predicting potential epitopes according to their predicted alleles. Results from the NetMHC (Buus et al., Tissue Antigens, 62(5):378-384 (2003) and Nielsen et al., Protein Sci., 12(5): 1007-1017 (2003)), and BIMAS (Parker et al., J. Immunol., 152:163-175 (1994)) and SYFPEITHI (Rammensee et al., Immunogenetics, 50:213-219 (1999)) algorithms are shown in Table 3. The NetMHC algorithm used a neural network approach to determine likely epitopes from protein sequence, calculated a predicted binding affinity to HLA molecules, and classified this binding as being strong ($IC_{50}$<50 nM), weak ($IC_{50}$>50 nM and <500 nM), or less than weak ($IC_{50}$>500 nM) (http://www.cbs.dtu.dk/services/NetMHC/, accessed Jan. 4, 2008). FIG. 4 summarizes how the polypeptides that were directly identified by MS were predicted by the NetMHC algorithm to bind with HLA molecules. Twenty-seven (22%) of the Vaccinia polypeptides identified by MS were predicted by the algorithm to be strong binders with another 49 (41%) predicted to be weak binding. Twenty-four polypeptides identified by MS/MS were not predicted by the algorithm, 23 because of excess length.

Additionally, a comparison was made of the list of identified Vaccinia polypeptides to Vaccinia epitopes, from all alleles, contained in the Immune Epitope Database and Analysis Resource (IEDB, http://www.immuneepitope.org/home.do, accessed Jan. 4, 2008) (Peters et al., Nat. Rev. Immunol., 7(6):485-490 (2007)). From the list of 116 directly identified polypeptides, 23 were an exact match to an IEDB database record, while another 7 polypeptides were contained within a Vaccinia epitope from the IEDB database. These results demonstrated both the complementary information provided by direct identification of epitopes by MS, and the limitations inherent in relying solely on computer algorithms for understanding the spectrum of polypeptides presented by natural infection.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for vaccinia epitope specific quantitation of CD8+ T cells, wherein said kit comprises an MHC class I tetramer for performing flow cytometry comprising a polypeptide selected from the group consisting of SEQ ID NOs: 1-82 and 83.

* * * * *

UNITED STATES PATENT AND TRADEMARK OFFICE
CERTIFICATE OF CORRECTION

PATENT NO. : 9,389,232 B2
APPLICATION NO. : 14/173550
DATED : July 12, 2016
INVENTOR(S) : Gregory A. Poland et al.

Page 1 of 1

It is certified that error appears in the above-identified patent and that said Letters Patent is hereby corrected as shown below:

In the Specification

Column 13, Line 24 (Seq ID 23 as presented in Table 2): "FQQKVLQEY" should read
-- VIRNEVNDTHY --

Column 13, Line 33 (Seq ID 32 as presented in Table 2): "RVFAPKDTWSVF" should read
-- RVFAPKDTESVF --

Column 15, Line 15 (Seq ID 48 as presented in Table 2): "IGKASQNSPKOXMVY" should read
-- IGKASQNPSKOXMVY --

Column 15, Line 39 (Seq ID 69 as presented in Table 2): "KQKGHNKFPVNF" should read
-- LQKGHNKFPVNF --

Signed and Sealed this
Twenty-seventh Day of February, 2024

Katherine Kelly Vidal
*Director of the United States Patent and Trademark Office*